United States Patent
Martin et al.

(10) Patent No.: US 11,414,635 B2
(45) Date of Patent: Aug. 16, 2022

(54) INTEGRATION OF THREE DIMENSIONAL CELL CULTURE SCAFFOLDS IN MICROFLUIDIC DEVICES BY DIRECT FIBER SPINNING

(71) Applicant: Saint Louis University, St. Louis, MO (US)

(72) Inventors: Robert Scott Martin, Kirkwood, MO (US); Chengpeng Chen, St. Louis, MO (US); Scott Allen Sell, St. Louis, MO (US)

(73) Assignee: Saint Louis University, St. Louis, MO (US)

(*) Notice: Subject to any disclaimer, the term of this patent is extended or adjusted under 35 U.S.C. 154(b) by 814 days.

(21) Appl. No.: 16/094,086

(22) PCT Filed: Apr. 18, 2017

(86) PCT No.: PCT/US2017/028127
§ 371 (c)(1),
(2) Date: Oct. 16, 2018

(87) PCT Pub. No.: WO2017/184595
PCT Pub. Date: Oct. 26, 2017

(65) Prior Publication Data
US 2021/0222104 A1    Jul. 22, 2021

Related U.S. Application Data

(60) Provisional application No. 62/324,073, filed on Apr. 18, 2016.

(51) Int. Cl.
*C12M 3/06* (2006.01)
*C12M 1/12* (2006.01)
*D01D 5/098* (2006.01)
*D01D 7/00* (2006.01)

(52) U.S. Cl.
CPC ............ *C12M 23/16* (2013.01); *C12M 25/14* (2013.01); *D01D 5/0985* (2013.01); *D01D 7/00* (2013.01)

(58) Field of Classification Search
CPC ..... C12M 23/16; C12M 25/14; D01D 5/0985; D01D 7/00; D01D 5/04; D01F 6/625
See application file for complete search history.

(56) References Cited

U.S. PATENT DOCUMENTS

| | | |
|---|---|---|
| 2007/0269481 A1 | 11/2007 | Li et al. |
| 2009/0227026 A1 | 9/2009 | Rapoport et al. |
| 2011/0081394 A1 | 4/2011 | Zussman et al. |
| 2011/0101571 A1 | 5/2011 | Reneker |
| 2012/0034461 A1 | 2/2012 | Stevens |

(Continued)

OTHER PUBLICATIONS

Li et al. Use of Electrospinning to Directly Fabricate Hollow Nanofibers with Functionalized Inner and Outer Surfaces. Small (2005), 1(1), 83-86. (Year: 2005).*

(Continued)

*Primary Examiner* — Sean C. Barron
(74) *Attorney, Agent, or Firm* — Stinson LLP

(57) ABSTRACT

Disclosed are fluidic devices and methods for preparing fluidic devices. More particularly, disclosed are fluidic devices having fiber scaffolds and methods for their preparation. Also disclosed are methods for culturing cells using the fluidic devices having fiber scaffolds.

12 Claims, 25 Drawing Sheets

(56) References Cited

U.S. PATENT DOCUMENTS

2013/0273589 A1 10/2013 Faris et al.
2015/0024967 A1 1/2015 Mohapatra et al.

OTHER PUBLICATIONS

Chen et al., Use of electrospinning and dynamic air focusing to create three-dimensional cell culture scaffolds in microfluidic devices; Analyst, Royal Society of Chemistry, 10 pages.

* cited by examiner

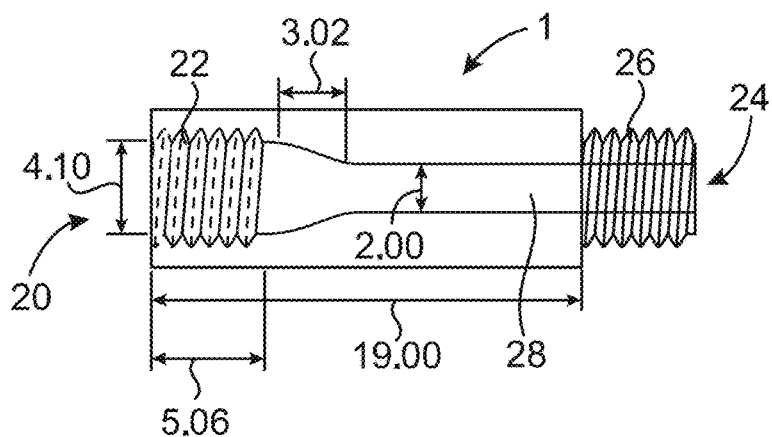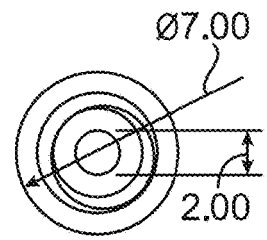
FIG. 5A
FIG. 5B
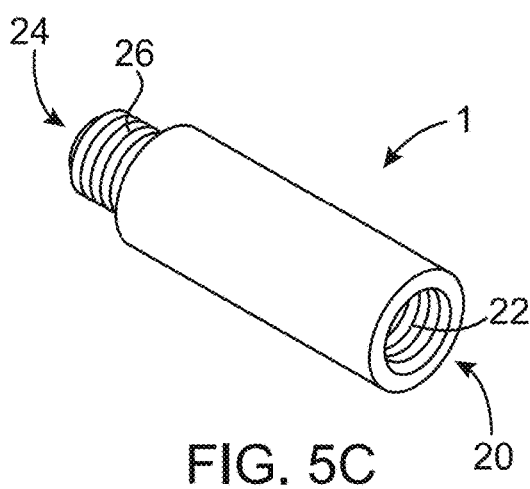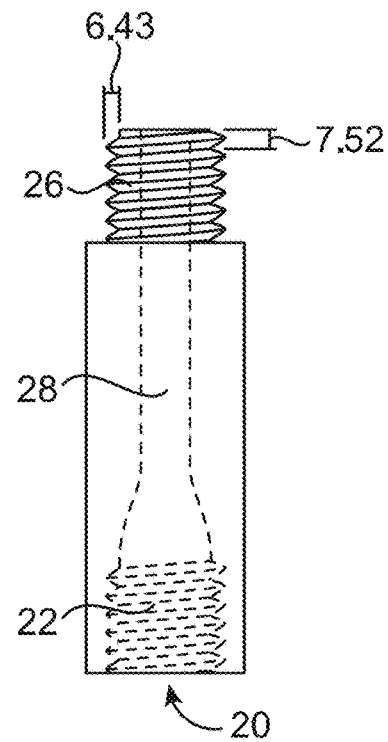
FIG. 5C
FIG. 5D

INTEGRATION OF THREE DIMENSIONAL CELL CULTURE SCAFFOLDS IN MICROFLUIDIC DEVICES BY DIRECT FIBER SPINNING

CROSS-REFERENCE TO RELATED APPLICATIONS

This application is a U.S. National Phase Application of PCT/US2017/028127 (published as WO 2017/184595), filed on Apr. 18, 2018, which claims priority to U.S. Provisional Patent Application Ser. No. 62/324,073, filed on Apr. 18, 2016, the disclosures of which are hereby incorporated by reference in their entireties.

STATEMENT REGARDING FEDERALLY SPONSORED RESEARCH OR DEVELOPMENT

This invention was made with government support under R15GM084470-04 awarded by the National Institutes of Health. The Government has certain rights in the invention.

BACKGROUND OF THE DISCLOSURE

The present disclosure relates generally to fluidics. More particularly, the present disclosure relates to fluidic devices including fiber scaffolds within fluidic channels and methods for preparing fluidic devices having spun fiber scaffolds within fluidic channels. The present disclosure further relates to cell culture methods using fluidic devices including fiber scaffolds.

The development of microfluidic technology has made it possible to integrate cells in microfluidic devices. With fluidic control, cell culture can be developed and integrated with on-chip-analysis. The concept of "Organs-on-a-Chip" represents a class of fluidic devices for in vitro cell culture, which can mimic key structures and functions of in vivo tissues and organs.

Compared to static cell culture, flow based cell culture provides not only continuous nutrient supply and waste removal, but also gradient control, mimicking in vitro physiological microenvironments (i.e. shear stress), and construction of a circulatory system that better represent in vivo conditions. It has been shown that flow-induced mechanical factors can affect the behaviors of many cell types, such as immune/inflammatory cells, stem cells, erythrocytes, endothelial cells and smooth muscle cells. This concept can be further developed to a Human-on-a-Chip, which integrates different in vitro organ models through a circulation mimic, for pharmacology and fundamental physiology studies. For example, a poly(dimethylsiloxane) (PDMS)-based lung-on-a-chip model was developed that contained multiple cell types to reconstitute the functional alveolar capillary interface of the human lung. Due to the reusability, ruggedness, and integrative properties, 3D-printed fluidic devices have recently emerged as platforms for in vitro cell studies and a few 3D-printed cells-on-a-chip models have been successfully developed. For example, a fluidic device containing pancreatic n-cells, endothelial cells and erythrocytes was recently reported, which enabled the investigation of cell-cell interactions between the three different cell types.

To construct an on-chip organ that is functional and representative of in vivo conditions, the first technical issue that needs to be addressed is the culture of cells in the fluidic device. However, most of the reported models cultured cells either on a bare polymer (e.g. PDMS) or in a microchannel with a layer of basement membrane proteins (i.e., collagens or fibronectin) adsorbed to its surface. It becomes more and more appreciated that flat surfaces may not represent the complex, three-dimensional extracellular matrix (ECM), where cells operate in vivo. However, limited research has been done to integrate ECM-resembling scaffolds within a fluidic device.

Electrospun scaffolds for in vitro cell culture have gained substantial academic interest. Some key features of electrospun fibers such as their non-woven fibrous structure, high porosity, spatial interconnectivity and high surface area closely resemble the characteristics of the native ECM. Electrospinning is a technique that processes polymer solutions into non-woven fibers with diameters on the micrometer to nanometer scale. A standard electrospinning system consists of a syringe with a metal cannula, a syringe pump, a high-voltage power supply and a grounded collector electrode. The electrospinning process can be easily performed in a laboratory setting, or scaled up for commercial applications. Briefly, when a polymer solution is drawn into a metal needle and charged with a large potential of, the electric field between the charged needle and the grounded collector electrode helps to overcome the surface tension of the droplet and generates a charged Taylor cone, which can be elongated by the electrostatic force. This cone whips through the air towards the collector, creating a dry fiber through evaporation of the solvent.

There have been many reports of successful application of electrospun fibers as in vitro cell culture matrices. For example, co-cultured smooth muscle cells and endothelial cells on electrospun fibers can proliferate and exhibit characteristic morphologies.

There are few reports showing the integration of electrospun fibers in a fluidic device, most of which are sandwiched models with a patch of electrospun fibers sealed between a substrate and a channel slab. However, certain sealing protocols (e.g. by thermal bonding) can potentially damage the structure of the electrospun fibers. In these models, electrospun fibers only reside on one side of a square channel, which limits the area and capacity for cell culture. Moreover, some techniques used in these reports, such as nano gold electrode array deposition are not readily available to every laboratory. It is also difficult to confine fibers into a small closed channel due to the vigorous whipping movement of fibers generated by electrospinning.

Accordingly, there exists a need for alternative methods for preparing fluidic devices having electrospun fibers in a fluidic channel as an in-channel cell culture scaffold, without sealing of slabs, or any other intricate procedures and techniques. Integrating electrospun fibers in a fluidic channel of devices enables cell culture on a scaffold similar to the native ECM with concomitant flow conditions to provide an ideal platform to study cells and tissues in vitro (FIG. 1A).

BRIEF DESCRIPTION OF THE DISCLOSURE

The present disclosure is related generally to fluidic devices. More particularly, the present disclosure relates to methods for preparing fluidic devices, including microfluidic devices, having spun fibers within fluidic channels.

In one aspect, the present disclosure is directed to a method for preparing a fluidic device comprising a fiber scaffold on an inner wall surface of the fluidic device, the method comprising: providing a fluidic device, the fluidic device comprising: an inlet end; an outlet end; an outer wall; an inner wall; and a channel, the channel defined therethrough by the inner wall and extending between the inlet end and the outlet end; and selectively coating an inner surface of the inner wall of the fluidic device by placing one of the inlet end or the outlet end of the fluidic device proximate to a cannula of a fiber spinning apparatus, wherein the fiber spinning apparatus comprises a gas sheath device; applying gas flow to the gas sheath device; pumping a polymer solution through the cannula of the fiber spinning apparatus to prepare a plurality of fibers; directing the fibers into the fluidic device, wherein the plurality of fibers form a fiber scaffold on the inner wall surface.

In another aspect, the present disclosure is directed to a cell culture method, the method comprising: providing a fluidic device, the fluidic device comprising: an inlet end; an outlet end; an outer wall; an inner wall; a fiber scaffold substantially coupled to an inner wall surface; and a channel, the channel defined therethrough by the inner wall and extending between the inlet end and the outlet end; contacting the fluidic device with a cell suspension, the cell suspension comprising a plurality of cells, wherein the plurality of cells adheres to the fiber scaffold; incubating the fluidic device with a cell suspension comprising a plurality of cells for a sufficient time that the plurality of cells adheres to the fiber scaffold; and culturing the plurality of cells.

In another aspect, the present disclosure is directed to a cell culture apparatus comprising a fluidic device, wherein the fluidic device comprises an inlet end; an outlet end; an outer wall; an inner wall, wherein the inner wall surface comprises a spun fiber scaffold; and a channel, the channel defined therethrough by the inner wall and extending between the inlet end and the outlet end.

In another aspect, the present disclosure is directed to a fluidic device comprising a fiber scaffold insert.

In accordance with the present disclosure, methods have been discovered that surprisingly allow for the direct integration of spun fibers in a channel of a fluidic device. The methods of the present disclosure have a broad and significant impact, as they allow for the direct integration of spun fibers into channels of fully formed fluidic devices. This is not possible with traditional methods that use sealing protocols to sandwich a patch of electrospun fibers between a substrate and a channel slab in part because of the vigorous whipping movement of fibers generated by electrospinning.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 5A is an illustration depicting an exemplary embodiment of a 3D-printed channel device and exemplary dimensions for the channel dimeter (2.0 mm), inlet diameter (4.10), length of thread region (5.06), transition length (3.02), channel length (15.0 mm) and total length. Units are in millimeters (mm). "A" depicts the thread dimensions.

FIG. 5B is a schematic illustration depicting a top view of an exemplary embodiment of a 3D-printed channel device and exemplary dimensions for the diameter at the inlet (7.00) and diameter of the channel (2.00). Units are in millimeters (mm).

FIG. 5C is a schematic illustration depicting a microfluidic device showing inlet end, outlet end and threading at the inlet and outlet.

FIG. 5D is a schematic illustration depicting a microfluidic device and exemplary dimensions for threading width (6.43) and threading height (7.52). Units are in millimeters (mm).

FIG. 20A depicts endothelial cells after a 24-hour static culture in a petri dish. FIG. 20B depicts endothelial cells cultured for 24 hours under flowing media (after the 24 hour static culture step). FIG. 20C depicts endothelial cells cultured for 48 hours under flowing media (after the 24 hour static culture step). Bright spots indicate cells stained by acridine orange, although the topography of the fibers prevents obtaining a uniform focal plane and some cells may be out of focus. FIG. 20D depicts cell counting results for the endothelial cells cultured under the three conditions mentioned above. Data indicates that after a 72-hour culture (24 hour static culture+48 hour culture in flowing media), the cells were still viable on the PS fibers without losing cell numbers While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, methods for directly depositing spun fibers in a channel of a fluidic device are disclosed. While the current design is focused on fluidic devices, the method itself is versatile and can be extended to other fluidic devices having fully formed channels where focusing spun fibers is necessary or desired.

As used herein, "selectively coating" refers to directing spun fibers emerging from the cannula of a fiber spinning apparatus into the inlet (or the outlet) of the fluidic device such that the spun fibers are deposited on the surface of the inner wall of the fluidic device.

In one aspect, the present disclosure is directed to a method for preparing a fluidic device comprising a fiber scaffold on an inner wall surface of the fluidic device, the method comprising: providing a fluidic device, the fluidic device comprising: an inlet end; an outlet end; an outer wall; an inner wall; and a channel, the channel defined therethrough by the inner wall and extending between the inlet end and the outlet end; and selectively coating an inner surface of the inner wall of the fluidic device by placing one of the inlet end or the outlet end of the fluidic device proximate to a cannula of a fiber spinning apparatus, wherein the fiber spinning apparatus comprises a gas sheath device; applying gas flow to the gas sheath device; pumping a polymer solution through the cannula of the fiber spinning apparatus to prepare a plurality of fibers; directing the fibers into the fluidic device, wherein the plurality of fibers form a fiber scaffold on the inner wall surface.

Spun fiber scaffolds can be prepared by electrospinning and blow spinning as described herein.

Electrospinning is a technique that utilizes polymer solutions to fabricate non-woven fibers with diameters on the micrometer to nanometer scale (ranging from single digit nanometer to hundreds of microns). A standard electrospinning system includes a syringe with a metal cannula, a syringe pump, a high voltage power supply and a grounded collector. When a polymer solution is drawn into the needle and charged with a large potential of ~20 kV, the electric field between the charged needle and the grounded collector electrode helps to overcome the surface tension of the droplet and generates a charged Taylor cone, which can be elongated by the electrostatic force. This cone whips through the air towards the collector, creating dry fibers through evaporation of the solvent.

Figure 1A:
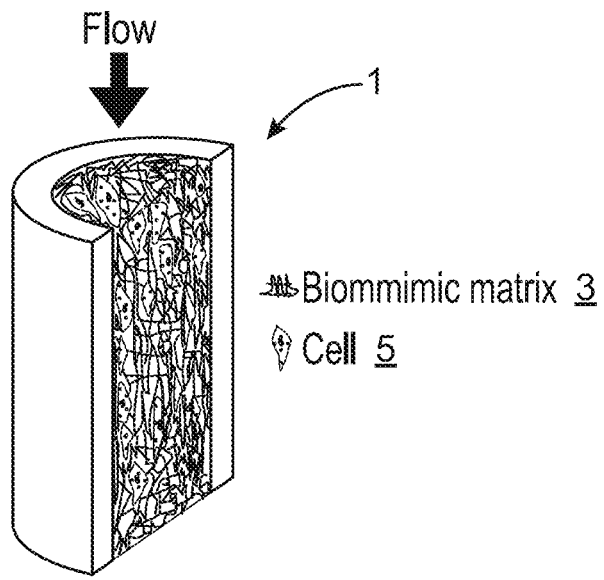
FIG. 1A is a schematic illustration of a cutaway of a fluidic device depicting an electrospun fiber scaffold coating the surface of an inner wall of the fluidic device with cells incorporated into the scaffold.
Figure 1B:
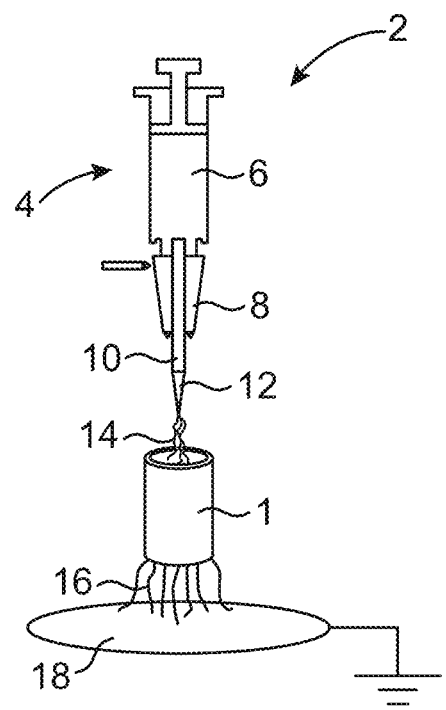
FIG. 1B is a schematic illustration of electrospinning with direct fiber focusing to coat the inner wall of the fluidic device.

Referring to FIG. 1A, fluidic device 1 includes a fiber scaffold 3 on an inner wall surface. Although FIG. 1A represents a fiber scaffold prepared by electrospinning, the fiber scaffold can be prepared by solution blown spinning as described herein. A cell 5 can be cultured in fluidic device 1 using fiber scaffold 3 as a substrate to which cell 5 attaches, migrates, proliferates and grows. Referring to FIG. 1B, exemplary embodiment of electrospinning apparatus 2 includes syringe 4 containing a polymer solution 6, a gas sheath device 8, and a cannula 10. Polymer solution 6 pumped through the cannula 10 of the syringe 4 forms a Taylor cone 12 to prepare a plurality of electrospun fibers 14. Electrospun fibers 14 are focused at the inlet of fluidic device 1 and fibers exiting 16 fluidic device 1 are directed to ground 18. As focused electrospun fibers 14 pass through fluidic device 1, the fibers contact the surface of the inner wall of fluidic device as illustrated in FIG. 1 (see also, FIG. 3C).

Figure 2A:
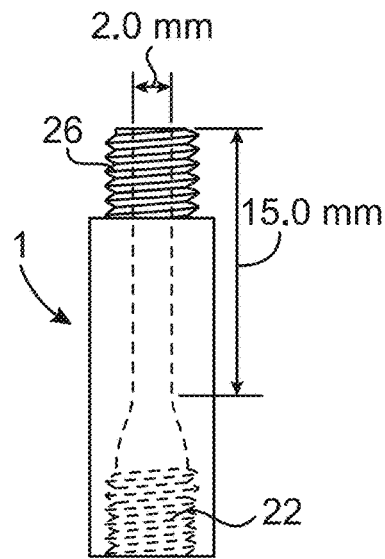
FIG. 2A is a schematic illustration depicting an exemplary embodiment of a 3D-printed fluidic device threaded inlet and outlet ports and exemplary dimensions for the channel dimeter (2.0 mm) and channel length (15.0 mm).

FIG. 2A depicts exemplary fluidic device 1 providing exemplary dimensions for channel diameter (2.0 mm) and the segment of channel (15.0 mm) having 2.0 mm diameter diameter. FIG. 2A further depicts threading 26 and 22 for attaching fluidic device 1 to additional components.

Figure 2B:
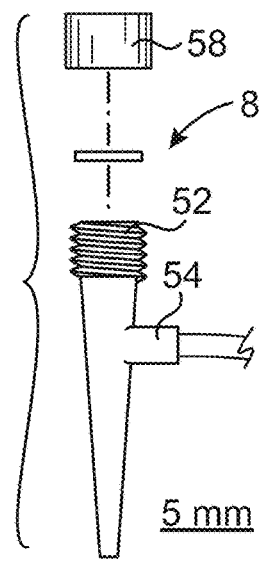
FIG. 2B is a schematic illustration depicting an exploded view of an exemplary embodiment of an air sheath device used with the electrospinning apparatus for direct fiber focusing. Scale bar=5 mm.
Figure 2C:
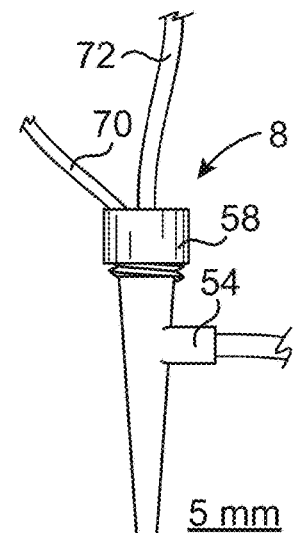
FIG. 2C is a schematic illustration depicting an assembled exemplary embodiment of an air sheath device connected to tubing and a cannula with an aluminum wire configured to be connected to a high voltage supply. Scale bar=5 mm.
Figure 2D:
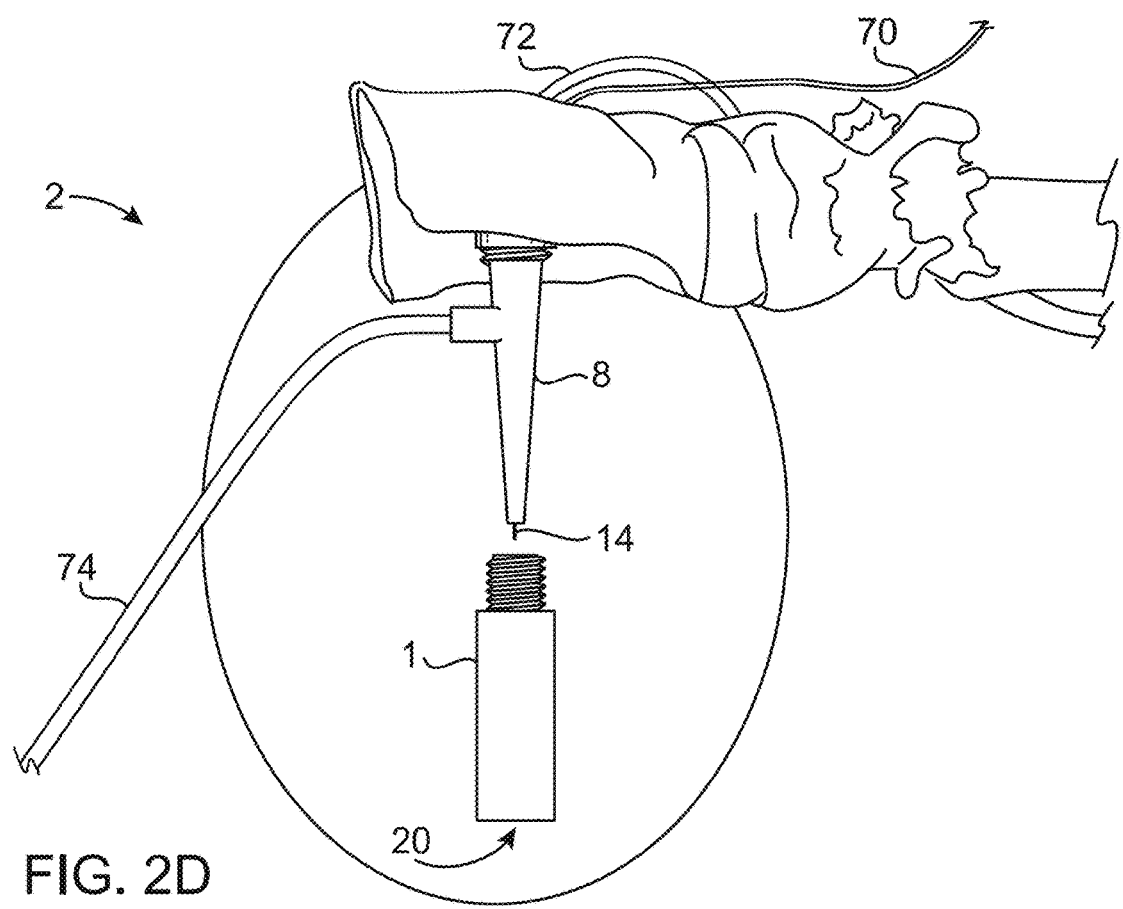
FIG. 2D is a schematic illustration depicting an exemplary embodiment of a setup for electrospinning fibers into a 3D-printed fluidic device.

Gas flow is applied to the gas sheath device 8; pumping a polymer solution 6 through the cannula 10 of the electrospinning apparatus 2 to prepare a plurality of electrospun fibers; directing the electrospun fibers into the inlet end of fluidic device 1, wherein the plurality of electrospun fibers form an electrospun fiber scaffold substantially coupled to the surface of the inner wall. FIG. 2B depicts an exploded view of exemplary gas sheath device 8 having threading 52 to removably couple gas sheath device 8 to cap 58. FIG. 2C depicts assembled view of gas sheath device 8 with cap 58 tightened and showing a portion of electrode 70, fluidic tubing 72 for applying polymer solution into device and gas tubing 74 entering side port 54. FIG. 2D depicts exemplary embodiment of fiber spinning device 2 using gas sheath device 8 to apply spun fiber scaffold to inner wall surface of fluidic device 1. FIG. 2D depicts fiber 14 exiting gas sheath device 8 and being directed to fluidic device 1 with inlet port 20 serving as exit for fibers during fiber scaffold application process. FIG. 2D further depicts electrode 70, fluidic tubing 72 for applying polymer solution and gas tubing 74.

In one embodiment, the inner surface includes a plurality of spun fiber scaffolds covering substantially all of the inner wall surface.

Referring to FIGS. 5A-5D, the inlet end 20 can further include threads 22. Including threads allows for attaching the fluidic devices of the present disclosure at the inlet end 20 to other devices and components. The outlet end 24 can further include threads 26. Including threads allows for attaching the fluidic devices of the present disclosure at the outlet end 24 to other devices and components. Threads 22 and 26 allow fluidic device to be independently and removably coupled to other devices and components. Channel 28 extends between inlet end 20 and outlet end 24. Channel 28 can include a constriction 30 whereby channel 28 changes in diameter.

Referring to FIGS. 9A-9E, gas sheath device 8 includes an inlet end 46, an outlet end 48 and a channel 50 therebetween. The inlet end 46 of gas sheath device 8 can be threaded 52 to reversibly couple gas sheath device to the electrospinning apparatus. Gas sheath device 8 is reversibly coupled to electrospinning apparatus whereby cannula 10 fits within the channel 50 of gas sheath device 8. Gas sheath device 8 can include a cap 58 having an aperture 60 through which cannula 10 can be inserted. Gas sheath device 8 also includes a side port 54 having a side inlet 56 through which gas flow is applied. Side inlet 56 is fluidly coupled to channel 50 such that gas flows through side inlet 56 into channel 50 and out through outlet end 48. As polymer solution exits cannula 10, the gas flow through outlet end 48 of gas sheath device 8 directs fibers exiting cannula 10 toward inlet end 20 of fluidic device 1.

In one aspect, the present disclosure is directed to a method for preparing a fluidic device comprising a fiber scaffold on an inner wall surface of the fluidic device. The method includes: providing a fluidic device, the fluidic device comprising: an inlet end, an outlet end, an outer wall, an inner wall, and a channel, the channel defined therethrough by the inner wall and extending between the inlet end and the outlet end; and selectively coating an inner surface of the inner wall of the fluidic device by placing the inlet end of the fluidic device proximate to a cannula of fiber spinning apparatus, wherein the fiber spinning apparatus comprises a gas sheath device; applying gas flow to the gas sheath device; pumping a polymer solution through the cannula of the fiber spinning apparatus to prepare a plurality of fibers; directing the fibers into the inlet end, wherein the plurality of spun fibers form a fiber scaffold substantially coupled to the surface of the inner wall.

In this embodiment, solution blown spinning generates fibers without the use of high voltage. A high velocity sheath gas is used to apply a focusing force to a pumped polymer solution, resulting in polymer stream that can subsequently expand into fine fibers that can be collected onto a non-grounded substrate. As described herein, as polymer solution exits cannula 10, the gas flow through outlet end 48 of gas sheath device 8 directs fibers exiting cannula 10 toward inlet end 20 of fluidic device 1.

The method can further include contacting the fluidic device with a cell suspension. As illustrated in FIG. 1, contacting the fluidic device 1 with a cell suspension allows for attachment of the cells 5 to the fiber scaffold 3.

The method can further include positioning the cannula of the electrospinning apparatus a distance from the inlet end of the fluidic device. In one embodiment, the cannula is positioned about 0 millimeters to about 5 millimeters from the inlet end of the fluidic device. In one embodiment, the cannula is positioned about 2 millimeters from the inlet end of the fluidic device.

The method can further include selectively coating the inner wall of the fluidic device. Particularly suitable coating cycles can range from 1 time to about 10 times. The inner wall of the fluidic device is selectively coated for a time ranging from about 1 second to about 20 seconds.

The deposited spun fiber scaffold thickness can suitably range from about 1 µm to about 500 µm. The deposited spun fiber scaffold thickness can be determined, for example, by measuring electron microscope images (as measured from cross-sectional views of the fluidic device from the inner surface of the channel toward the center of the channel as shown in FIG. 3C, for example). A single coating cycle results in a single spun fiber scaffold layer that can be coated layer-by-layer any number of desired times until reaching a desired spun fiber scaffold thickness. For example, 1 coating cycle would result in a single fiber scaffold coating the inner wall surface of the fluidic device. Ten (10) coating cycles, for example, would result in 10 fiber scaffold layers the inner wall surface of the fluidic device. The number of cycles and the timing of coating can be performed alone or in combination to achieve fiber scaffold layers of desired thickness.

The spun fiber diameter size can range from tens of nanometers in diameter to micrometers in diameter. For example, spun fiber diameter size can range from about 10 nm to about 2.5 µm. Suitably, the spun fiber size in the scaffold can range from about 0.1 µm to about 1 µm. The fiber diameter size can be determined, for example, by measuring electron microscope images.

The pore size of the spun scaffold can range from about 90 µm$^2$ to about 135 µm$^2$. Pore size can be determined by measuring electron microscope images.

The method can further include a drying step. Drying can be accomplished by air drying the coated device. Alternatively, drying can be accomplished by blowing gas into the channel.

Any fluidic device having a channel as described herein can suitably be employed for focusing spun fibers to prepare spun fiber scaffolds within a channel Advantageously, the methods of the present disclosure allow for focusing spun fibers into preformed channels as compared to assembling different parts of a device to sandwich a scaffold within a channel formed after the device is assembled. The methods of the present disclosure also advantageously results in substantially coating the entire surface of the inner wall defining the channel as compared to coating one surface of an unassembled device. Suitable fluidic devices include for example, microfluidic devices and nanofluidic devices. Particularly suitable exemplary fluidic devices described in the present disclosure can be prepared using processes including 3D-printing fluidic devices and poly(dimethylsiloxane) microfluidic devices (soft lithography). Other suitable fluidic devices can be fabricated using processes such as, for example, photolithography, glass, ceramics and metal etching, deposition and bonding, injection molding, and "ESCARGOT" (embedded scaffold removing open technology, which uses a dissolvable scaffold within a single block of PDMS, for example).

Figure 10A:
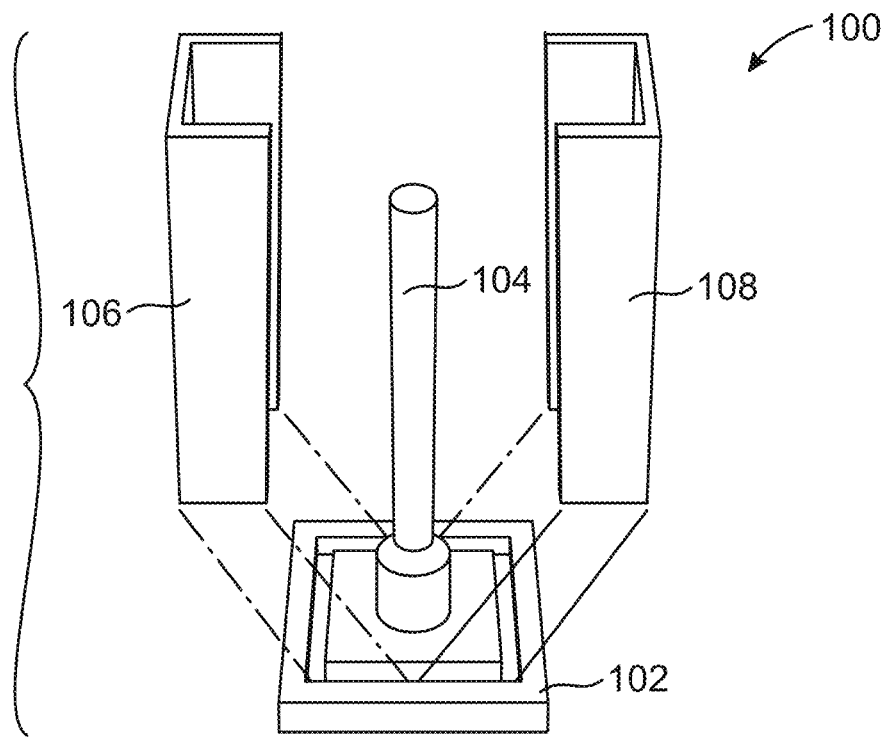
FIG. 10A is a schematic illustration depicting an exploded view of an exemplary 3D-printed mold for preparing a PDMS fluidic device in its disassembled configuration.
Figure 10B:
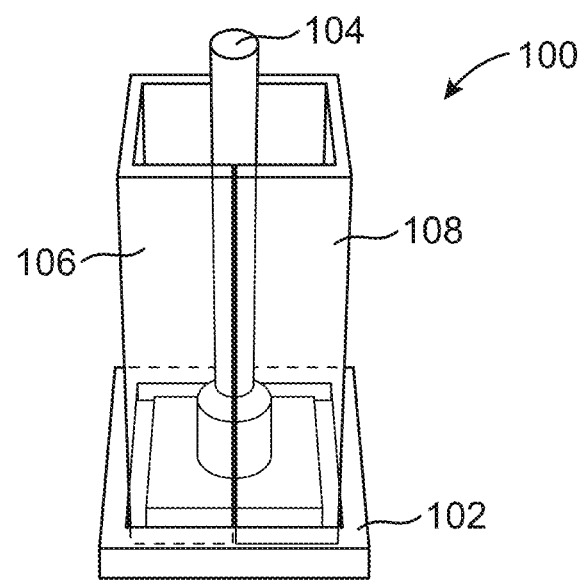
FIG. 10B is a schematic illustration depicting an exemplary 3D-printed mold for preparing a PDMS fluidic device in its assembled configuration.
Figure 10C:
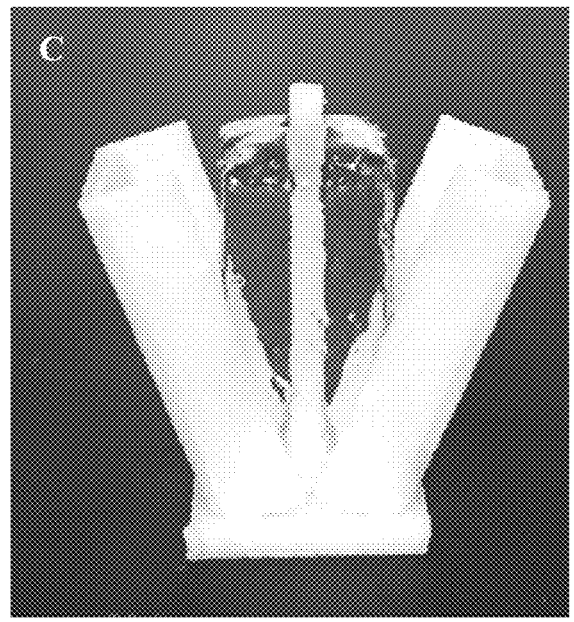
FIG. 10C is a photograph depicting an exemplary 3D-printed mold for preparing a PDMS fluidic device showing the PDMS device in the 3D-printed mold after polymerization with the channel-forming post through the center of the polymerized PDMS material.

FIGS. 10A-10D depict an exemplary embodiment using soft lithography to form a transparent fluidic device. FIG. 10A shows an exploded (disassembled configuration) view of a 3-part mold 100 having a base 102 with central post 104, a first side 106 and a second side 108. Base 102 includes grooves (slots) for reversibly coupling first 106 and second 108 sides when assembled as shown in FIG. 10B. FIG. 10C is a photograph of a partially disassembled 3-part mold having first side and second side positioned away from fluidic device. Central post of base extends centrally through fluidic device. As shown in photograph depicted in FIG. 10D, when fluidic device is completely removed from 3-part mold, a channel previously occupied by central post of the mold is formed when the central post of the mold is removed from fluidic device.

Suitable spun material for fiber scaffold preparation can be a synthetic polymer, a natural protein, and combinations thereof. The device can include spun fibers of a single type of spun material and combinations of spun fibers of different types of spun materials.

Suitable synthetic polymers can be, for example, polycaprolactone (PCL), polydioxanone (PDO), poly (glycolic acid) (PGA), poly(L-lactic acid) (PLA), poly(lactide-co-glycolide) (PLGA), poly(L-lactide) (PLLA), poly(D,L-lactide) (P(DLLA)), poly(ethylene glycol) (PEG), poly(ε-caprolactone) (PCL), montmorillonite (MMT), poly(L-lactide-co-ε-caprolactone) (P(LLA-CL)), poly(ε-caprolactone-co-ethyl ethylene phosphate) (P(CL-EEP)), poly[bis(p-methylphenoxy) phosphazene] (PNmPh), poly (3-hydroxybutyrate-co-3-hydroxyvalerate) (PHBV), poly (ester urethane) urea (PEUU), poly(p-dioxanone) (PPDO), polyurethane (PU), polyethylene terephthalate (PET), poly (ethylene-co-vinylacetate) (PEVA), poly(ethylene oxide) (PEO), poly(phosphazene), poly(ethylene-co-vinyl alcohol), polymer nanoclay nanocomposites; a halogenated polymer solution containing metal compounds (e.g., graphite); poly (ethylenimine), grafted cellulosics, poly(ethyleneoxide), and poly vinylpyrrolidone; polystyrene (PS) and combinations thereof.

Suitable natural proteins can be, for example, silk fibroin, collagen, alginate, elastin, hyaluronic acid, gelatin, fibrinogen, chitin, chitosan, fibronectin and combinations thereof.

In another aspect, the present disclosure is directed to a cell culture method, the method comprising: providing a fluidic device, the fluidic device comprising: an inlet end; an outlet end; an outer wall; an inner wall; a fiber scaffold substantially coupled to an inner wall surface; and a channel, the channel defined therethrough by the inner wall and extending between the inlet end and the outlet end; contacting the fluidic device with a cell suspension, the cell suspension comprising a plurality of cells, wherein the plurality of cells adheres to the fiber scaffold; incubating the fluidic device with a cell suspension comprising a plurality of cells for a sufficient time that the plurality of cells adheres to the fiber scaffold; and culturing the plurality of cells.

The method can further include circulating culture medium through the channel of the fluidic device. Culture medium can be circulated through the channel of the device by coupling tubing in flow communication with the inlet end and the outlet end of the fluid device. Flow of the culture medium can be performed using by connecting the tubing with a pumping mechanism such as a peristaltic pump. Preferably, the flow rate ranges from about 1 µL/minute to about 500 µL/minute. The flow rate of the culture medium can be adjusted as desired depending on the experimental parameters being investigated. For studies including shear stress response by cells cultured in the fluidic device, the flow rate can be increased above 500 µL/minute. Although the flow rate can be increased to a flow rate that results in shearing cells from the spun fiber scaffold, it is generally desirable to adjust the flow rate below which cells are sheared from the spun fiber scaffold.

In another aspect, the present disclosure is directed to a cell culture apparatus comprising a fluidic device, wherein the fluidic device comprises an inlet end; an outlet end; an outer wall; an inner wall, wherein the inner wall surface comprises a spun fiber scaffold; and a channel, the channel defined therethrough by the inner wall and extending between the inlet end and the outlet end.

Spun fiber scaffolds can be prepared by electrospinning and blow spinning as described herein.

The deposited spun fiber scaffold thickness can suitably range from about 1 µm to about 500 µm, as described herein. The deposited spun fiber scaffold thickness can be determined, for example, by measuring electron microscope images, as described herein.

The spun fiber diameter size can range from tens of nanometers in diameter to micrometers in diameter, as described herein. For example, spun fiber diameter size can range from about 10 nm to about 2.5 µm. Suitably, the spun fiber size in the scaffold can range from about 0.1 µm to about 1 µm. The fiber diameter size can be determined, for example, by measuring electron microscope images, as described herein.

The pore size of the spun scaffold can range from about 90 µm$^2$ to about 135 µm$^2$, as described herein. Pore size can be determined by measuring electron microscope images, as described herein.

The cell culture apparatus can further include a plurality of cells. Any suitable cell type known to those skilled in the art can be used in the culture methods. Suitable cells include, for example, fibroblasts, endothelial cells, erythrocytes, smooth muscle cells, pancreatic cells, lung cells, bone cells (e.g., osteocytes, osteoblasts, osteoclasts), chondrocytes, neuronal cells, polymorphonuclear cells (e.g., neutrophils, eosinophils, basophils), agranular leukocytes (e.g., monocytes, lymphocytes), macrophages, B-cells, T-cells, NK cells, stem cells of any lineage (e.g., embryonic, mesenchymal, hematopoietic, etc.), hepatocytes and combinations thereof. The plurality of cells can include a mixture of different cell types. For example, cells such as for example, endothelial cells and smooth muscle cells can be co-cultured in the fluidic devices.

The inlet end of the fluidic device of the cell culture apparatus can further include threads to enable coupling of the fluidic device to additional devices and components, as described herein. Additional components include, for example, tubing, gas ports, compressed gas lines, gas sheath devices. The outlet end of the fluidic device of the cell culture apparatus can further include threads to enable coupling of the fluidic device to additional devices and components, as described herein. Additional devices and components include, for example, tubing, gas ports, compressed gas lines, gas sheath devices.

In another aspect, the present disclosure is directed to fluidic devices having fiber scaffold inserts. The fluidic devices having fiber scaffold inserts are particularly useful in cell culture applications.

Figure 12:
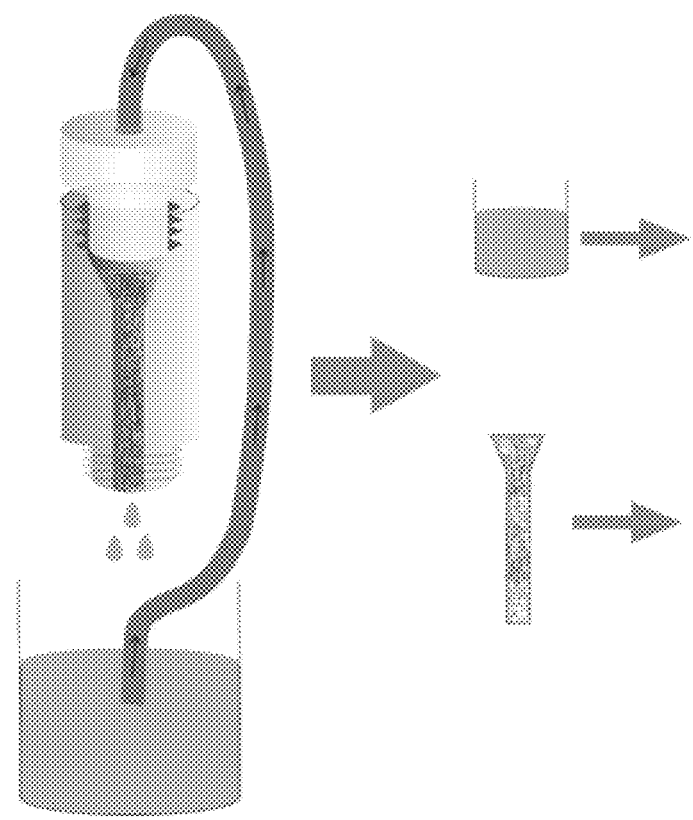
FIG. 12 is a schematic depicting use of fluidic devices having fiber scaffold inserts in cell culture applications.
Figure 15A:
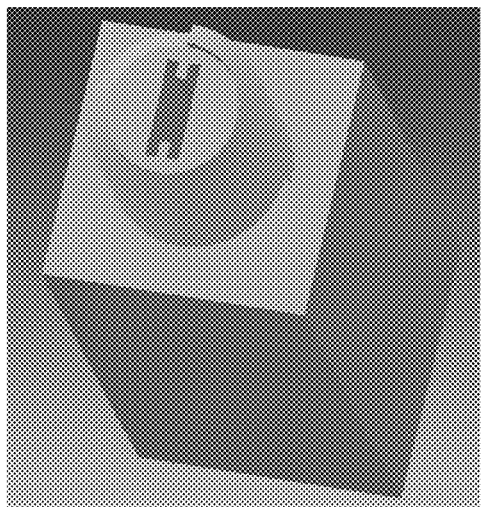
FIG. 15A depicts an embodiment of a fluidic device having two slots for positioning fibrous scaffold inserts.
Figure 15B:
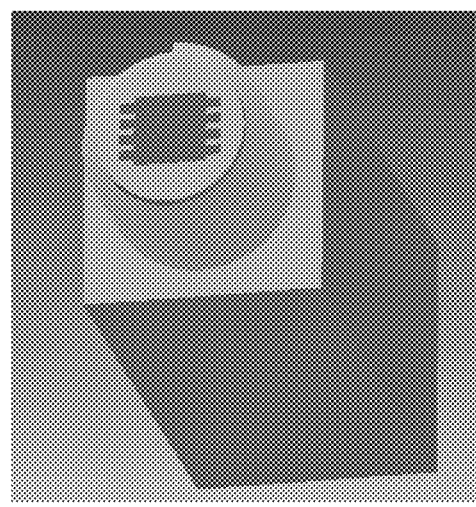
FIG. 15B depicts an embodiment of a fluidic device having four slots for positioning fibrous scaffold inserts.

Referring to FIG. 12, to prepare fluidic devices having fiber scaffold inserts, fiber scaffolds can be prepared on a flat surface (a collection support material). After deposition of the fiber scaffold on a collection support material, the fiber scaffold on the collection support material is cut to a desired shape to form fiber scaffold inserts that are inserted into a fluidic device. A single fiber scaffold insert and a plurality of fiber scaffold inserts can be inserted into a fluidic device. When two or more fiber scaffold inserts are inserted, the fiber scaffold inserts can be stacked in a side-by-side manner. In the first step, fiber scaffolds are deposited on a collection support material. The collection support material with the fiber scaffold is then cut into any desired shape. Suitable shapes include a shape that matches the fluidic device channel. FIG. 12 is a schematic illustration depicting the fluidic device with fiber scaffold inserts in a recirculating culture medium cell culture system. Culture media flowing out of the fluidic device and cells cultured in the fiber scaffold inserts can be analyzed by downstream methods (FIG. 12). Embodiments of the fluidic device for housing fiber scaffold inserts include, for example, a single slot and a plurality of slots for housing fiber scaffold inserts. Embodiments of the fluidic device for housing fiber scaffold inserts include, for example, a single slot that can house one fiber scaffold insert. Embodiments are also contemplated in which a single slot can house a plurality of fiber scaffold inserts. Embodiments are also contemplated having a plurality of slots that can house one or more fiber scaffold inserts in each slot. FIGS. 15A and 15B, illustrate exemplary fluidic devices having two slots and four slots. Any desired number of slots can be included in the fluidic devices.

Any support material can be used to collect the fibers to prepare fiber scaffold inserts. The collection support material for collecting fiber scaffolds can be plastic, paper, and metal materials. Suitable collection support material can be plastic (e.g., polycarbonate, etc.) films. Other suitable collection support material includes polyester and polystyrene sheets.

The fluidic device having the fiber scaffold can then be coupled with other devices and components as described herein (and shown in FIG. 12). Examples of other devices and components include absorbance detection modules, fluorescence detection modules, luminescence detection modules, light scattering detection modules, electrochemical detection modules, conductivity detection modules, mass spectrometry interfaces, chromatography interfaces, electrophoresis interfaces, nebulization interfaces (for interface with atomic spectroscopy or inductively coupled plasma), and combinations thereof.

Figure 14A:
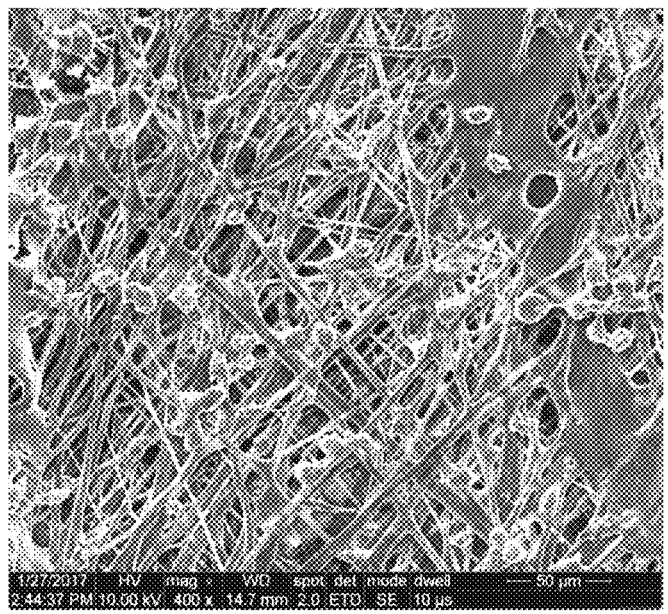
FIG. 14A is an electron micrograph showing the morphology of macrophages cultured on fibrous scaffold inserts.
Figure 14B:
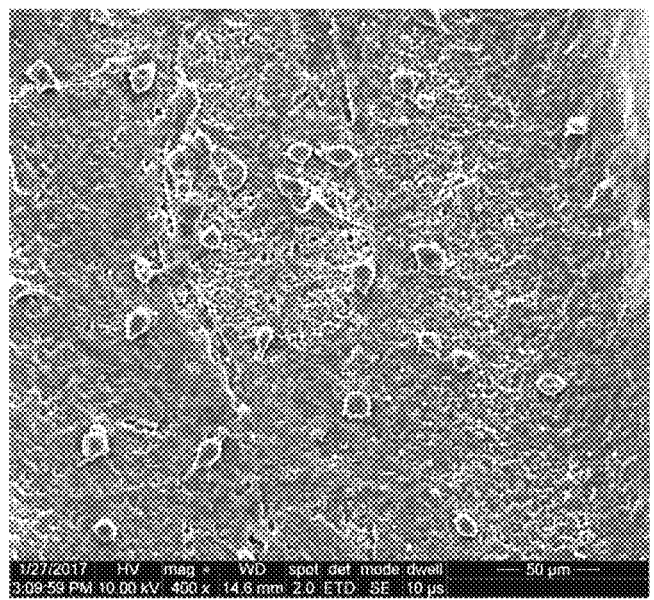
FIG. 14B is an electron micrograph showing the morphology of macrophages cultured on flat (non-fibrous) inserts.

The fluidic devices having the fiber scaffold inserts can further be seeded with a cell and used in culture process. As disclosed herein, any cell type can be used to seed the fluidic device. As also disclosed herein, mixtures of cell types can be used to seed the fluidic device. FIGS. 14A and 14B show the morphology of macrophages cultured on fibrous scaffold inserts and flat (non-fibrous) inserts.

As shown in FIGS. 15A and 15B, fluidic devices can include slots. The slots can guide the positioning of the fiber scaffold inserts into the channel of the fluidic devices. The slots can also maintain separation between individual fiber scaffold inserts such that individual fiber scaffold inserts are not in direct contact with other fiber scaffold inserts.

The fiber diameter size can range from tens of nanometers in diameter to micrometers in diameter. For example, fiber diameter size can range from about 10 nm to about 2.5 µm. Suitably, the fiber size in the scaffold can range from about 0.1 µm to about 1 µm. The fiber diameter size can be determined, for example, by measuring electron microscope images.

The pore size of the fiber scaffold can range from about 90 µm$^2$ to about 135 µm$^2$. Pore size can be determined by measuring electron microscope images.

The method can further include a drying step. Drying can be accomplished by air drying the fiber scaffold on the collection substrate.

The disclosure will be more fully understood upon consideration of the following non-limiting Examples.

EXAMPLES

Example 1

In this Example, the fabrication of a 3D-printed fluidic device and a 3D-printed air sheath device is described.

The 3D-devices were designed using Autodesk Inventor Professional 2015 (San Rafael, Calif., USA). The standard tessellation language file (.STL file) was used by the 3D-printer (Objet Eden 260 V, Stratasys, Ltd, Edina, Minn., USA) to create the devices. The material used in this work was called Full Cure 720 (Stratasys, Ltd, Edina, Minn., USA), the composition of which is propriety, but approximately containing 10-30% isobornyl acrylate, 10-30% acrylic monomer, 15-30% acrylate oligomer, 0.1-1% photo initiator, as is provided on the Stratasys website. The devices were translucent upon being printed. The assembly schematics of the devices, with design details and dimensions, are shown in FIG. 5.

A male threaded part and a female threaded port (which fits commercial finger tight adapters) were designed on the fluidic device for easy connection to other devices/instruments (FIG. 2A). The air sheath consisted of a cone with a side connection port to air tanks, and a ring lid (open on the top). Threads were printed on both parts so that they can be simply integrated with each other, with septa in between. A metal cannula (300 µm i.d.×550 µm o.d., New England Small Tube Company, NH, USA) connected to a piece of Tygon tubing (0.02"i.d.×0.06" o.d., Cole-Parmer, IL, USA) was placed through the air sheath, together with a piece of aluminum wire that was connected to a high voltage supply (FIG. 2B).

Example 2

In this Example, electrospinning fibers into a fluidic device is demonstrated.

The polycaprolactone (PCL) polymer (M.W.80,000, Sigma-Aldrich, MO, USA) was dissolved in 1,1,1,3,3,3-Hexafluoro-2-propanol (HFP) at room temperature. The concentration of PCL used in this study was 15% (w/v). After the polymer solution was homogenized on a shaker, it was loaded in a 5 mL syringe fitted with a piece of Tygon tubing (0.02" i.d.×0.06" o.d., Cole-Parmer, IL, USA) via commercial adapters (IDEX, CA, USA). A steel cannula (300 µm i.d.×550 µm o.d., New England Small Tube Company, NH, USA) was connected at the end of the Tygon tubing and was placed through the air sheath. A piece of aluminum wire was coiled around the pin and connected to a 25 kV supply. The side port of the air sheath was connected to an air tank and 10 psi of air flow was applied to dynamically focus fibers coming out of the cannula. Once started, the polymer solution was driven by a syringe pump at a flow rate of 80 pL/min A 3D-printed fluidic device or a PDMS-based device was placed about 2 mm below the cannula to collect fibers. The devices were coated 5 times, with each coating lasting 10 seconds. After each coating, compressed air was blown through the channel for 10 seconds, to help dry the coated fibers. FIG. 2D shows the process to deposit fibers on the inside of a 3D-printed fluidic device.

Example 3

In this Example, fibers deposited in a microfluidic channel by electrospinning were characterized.

The coated fluidic device was split in half along the channel using a blade, which was then sputter coated with gold at 30 mA for 40 sec (Denton Vacuum LLC, Ni, USA). The sputter coated piece was then examined by a scanning electron microscope (SEM, Inspect F50 model, EEl, OR, USA) at 10 kV acceleration voltage. The fiber and pore sizes were analyzed using the lmageJ software. For each SEM image, at least 50 fibers were measured.

Example 4

In this Example, culture of human dermal fibroblasts (HDFs) on fiber coated 3D-printed fluidic devices was investigated.

Three fiber coated devices were connected end to end by the integrated threads (the male part connected to the threaded port of another device) and then soaked in isopropanol (IPA) for 12 hours. The devices were then taken out of IPA and placed in UV light in a cell hood for 24 hours. A 15 mL plastic test tube was processed as a container for cell culture on the fiber coated devices. A 0.5 cm diameter hole was drilled through the cap of the test tube, and a piece of 0.4 µm pore size polycarbonate membrane (Sigma-Aldrich, MO, USA) was sealed between the tube and the opened cap. This container was also sterilized by soaking it in IPA (12 hours) and drying it in UV light (24 hours).

Figure 6A:
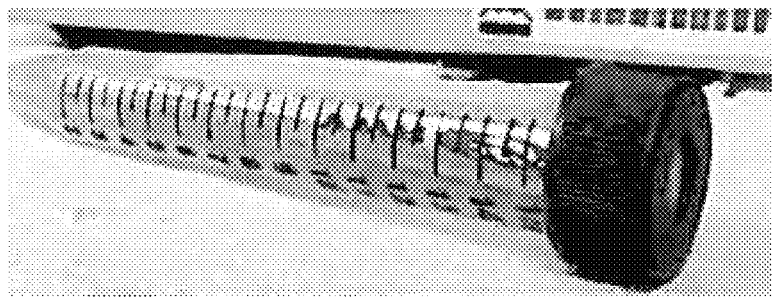
FIG. 6A is a photograph of a test tube holding three channel devices connected end-to-end by the integrated threads for seeding cells.
Figure 6B:
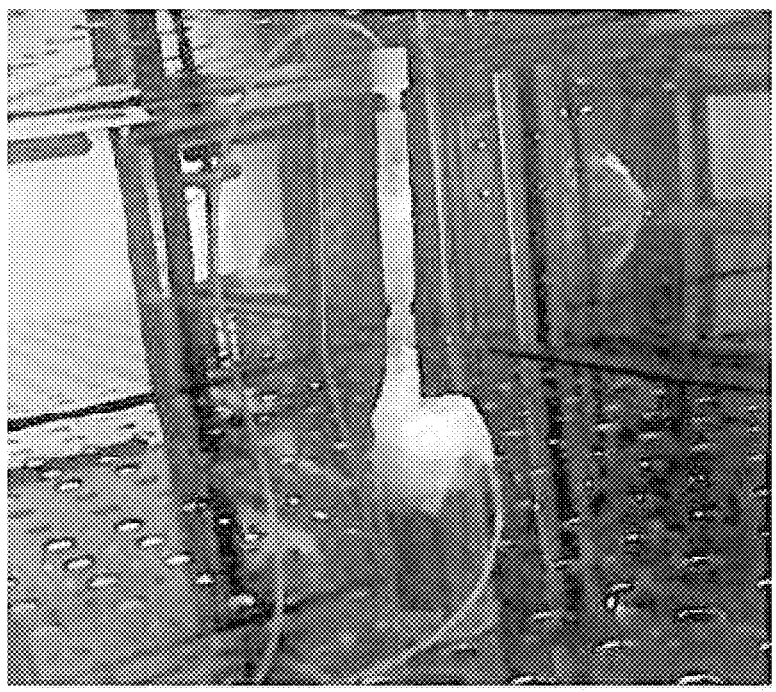
FIG. 6B is a photograph depicting the dynamic culture of cells in a vertically positioned device over a glass vial filled with culture media. Tubes in flow connection with the device allow for continuous flow of culture media through the device via a peristaltic pump.

Primary Human dermal fibroblasts (HDF, normal, human, adult, ATCC, VA, USA) with passage numbers of 1 to 4 were used in this study. When the cells were confluent in a T-75 flask, the DMEM/F-12 media buffered with 10% fetal bovine serum and 1% antibiotic-antimycotic (ThermoFisher Scientific, MO, USA) was removed and 7 mL trypsin/EDTA solution (ThermoFisher Scientific, MO, USA) was added. The flask was then placed in an incubator (37° C., 5% $CO_2$) for 5 minutes for the cells to be detached. The cell suspension was transferred into a 15 mL plastic test tube, which was then centrifuged at 1500 g for 5 minutes to pellet the cells. The supernatant in the test tube was removed without disturbing the pellet, after which, the cells were resuspended in 2 mL fresh media. An aliquot of 100 µL of the suspension was pipetted into a 700 µL centrifuge tube, followed by adding 100 µL buffered trypan blue solution (ThermoFisher, MO, USA). The amount of viable cells was then determined using a hemocytometer. The 2 mL cell suspension was further diluted to a density of 1 million viable cells per mL. There was usually 5 to 6 mL diluted cell suspension acquired after these steps. The diluted cell suspension was then transferred into the sterilized and dried test tube, followed by soaking the 3D-printed devices in the suspension. The test tube was recapped with a piece of porous membrane in between, which facilitates gas exchange between the media and the incubator atmosphere. The test tube was then placed horizontally in an incubator (37° C., 5% $CO_2$) for 12 hours (FIG. 6A), during which, the test tube was periodically rotated every 1 hour to make sure cells can adhere all around the channel, instead of only on one side. After the 12-hour static culture, the devices were placed vertically over a glass vial filled with fresh media. The end of the top device was connected via a commercial finger-tight fitting to a piece of Tygon tubing (0.02" i.d.×0.06" o.d., Cole-Parmer, IL USA), which went around the roller of a peristaltic pump (Cole-Parmer, IL, USA). The other end of the Tygon tubing was immersed in the media in the vial. The peristaltic pump circulated the media (at a flow rate of 400 µL/min) through the devices for another 24 hours in the incubator (FIG. 6B).

Example 5

In this Example, cells cultured in the 3D-printed fluidic device were evaluated using an MTS cell proliferation assay.

Figure 7:
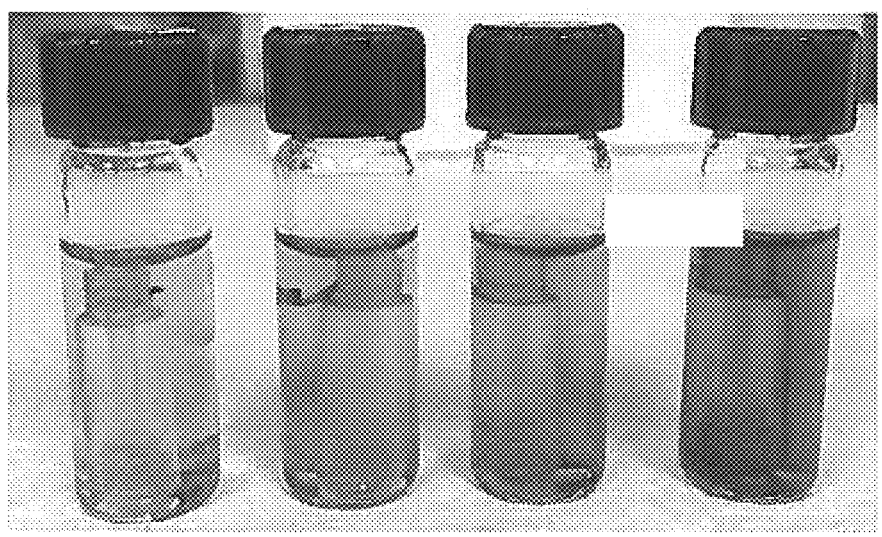
FIG. 7 is a photograph depicting vials containing devices with increasing amounts of viable fibroblasts from left to right for analysis by MTS assays. The more intense color illustrated more viable cells in the vial.

A CELLTITER96® MTS assay kit (Promega, WI, USA) was used to determine the number of viable cells in proliferation cultured on the 3D-printed fluidic device. The assay was prepared by mixing 5 mL MTS solution and 250 µL PMS solution from the kit. After the cell culture process was finished, the stringed devices were detached and each device was placed immediately in a glass vial containing 2 mL warmed fresh media. An aliquot of 500 µL assay solution was then added to each vial, followed by a thorough mixing. The vials were placed in an incubator (37° C., 5% $CO_2$) for 1 hour. The caps of the glass vials were loosened during the incubation to facilitate $O_2$ and $CO_2$ exchange between the media and the incubator atmosphere. Four standards were prepared to quantify viable cells in proliferation. HDFs cultured in a flask were trypsinized and resuspended as described above. Then different amounts of cell suspension were added into four glass vials, followed by adding fresh media to make a total volume of 2 mL in each vial. In the example of FIG. 7, the four vials contained 0, $0.40×10^5$, $1.56×10^5$, $4.76×10^5$ cells. Four bare fluidic devices were placed in the vials, to compensate for possible absorption/adsorption of the colored molecules in MTS assay onto the plastic of the fluidic devices. An aliquot of 500 µL of assay solution was then added to each vial, followed by a thorough mixing. The vials were incubated in the same way as described above.

After incubation, an aliquot of 50 µL of solution was sampled from each vial and loaded in a 96 well plate, followed by an absorption measurement at 490 nm using a plate reader (Molecular Devices LLC, CA, US). The absorbance values of the four standards were plotted versus cell amount, which was used as a calibration curve to quantify the amount of viable cells cultured on a fluidic device.

Example 6

In this Example, cells cultured in the 3D-printed fluidic device were evaluated using scanning electron microscopy (SEM).

After cell culture was finished, a fluidic device was split in half along the channel direction using a blade. The split pieces were soaked in 10% formalin (buffered in phosphate buffer solution) for 30 minutes at room temperature. The pieces were then soaked in sequence with 50%, 70%, 80%, and 95% ethanol for 10 minutes each, followed by two 10 minute rinses in 100% ethanol (Sigma Aldrich, MO, US). After the pieces were air dried, they were sputter coated with gold at 30 mA for 40 seconds, followed by SEM imaging.

Results

Liquid manipulation and micro-fabrication techniques have made it possible to culture cells under flow conditions. As aforementioned, compared to static cell culture, flow-based cell culture can be a step forward to better represent in vivo microenvironments (i.e., shear stress) and conditions (i.e., continuous nutrient supply and waste removal) for cell studies. The term "Organs-on-a-Chip" has been proposed recently to recapture the main functions of certain organs on a fluidic device, which can be potentially useful for applications such as drug toxicity assessment, drug screening, and fundamental physiological studies. Although flat cell culture matrices such as collagen and fibronectin layers have been widely applied on microfluidic devices for cell culture, little research has been done to incorporate in vivo representative extracellular matrix (ECM) in a fluidic device. Cells and tissues are embedded within three dimensional, fibrous ECM in vivo, which have proven to be able to regulate cellular activities. In other words, even under flow conditions, if cells are not cultured on an ECM-resemble scaffold, they may not be able to mimic in vivo conditions well.

Due to the high surface area to volume ratio, porosity and biocompatibility, spun fibers have become an ideal scaffold for ECM mimicking in many studies. Even though there are few reports trying to integrate spun fibers in a fluidic device with intricate techniques and procedures, there lacks a simple and direct way to combine such fibers within a fluidic channel. The results presented herein provide a new and simple method to directly coat spun fibers on the inside of a fully sealed fluidic channel. With traditional electrospinning techniques using an electric field is the primary driving force, fiber deposition tends to be widespread with large amounts of overspray that cannot be confined into small, closed fluidic channels. As described herein, the air dynamic focusing method focuses spun fibers such that inner walls of fluidic devices forming a channel can be substantially coated with spun fibers (as illustrated in FIG. 1B). Compared with a classical electrospinning setup, an air sheath placed around the metal cannula so that air flow can be applied to focus the fibers into a fluidic device. As shown in FIG. 2B, the air sheath device can conveniently be fabricated by 3D-printing, consisting of two parts: a cap and a cone with a side port. The two parts can be joined by the printed threads, with a piece of septa in between. The top of the cap is open so that a steel pin at the end of a piece of Tygon Tubing, as well as an aluminum wire (coiled on the cannula) can be placed through the air sheath (FIG. 2C). The side port acts as the sheath air inlet after being connected to a compressed air line. The sheath air velocity was determined to be between 2.9 and 3.4 m/s (corresponding pressures are 10 and 15 psi). The o.d. of the steel cannula was 550 µm, and the air sheath tip size was determined to be 800 µm in diameter.

As shown in FIG. 2D, a 3D-printed fluidic channel was utilized for coating with electrospun fibers. 3D-printing enabled the integration of a threaded port and a male threaded part on the device (FIG. 2A), which allows for convenient connection to other devices and instruments. After fibers were formed at the tip of the cannula, the sheath air focused the fibers going through the fluidic device. The exiting fibers from the end of the fluidic device distal to the electrospinning apparatus indicated successful coating of fibers on the inside of the fluidic channel. It was observed that without the sheath air the fibers randomly flowed around the device, and not into the channel at all. To obtain sufficient fibers on the inside of a channel, the channel can be coated multiple times. Under the experimental conditions described herein, coating the device 5 times, with each coating lasting 10 seconds, provided sufficient fibers. To avoid the formation of welded fibers that may reduce the porosity and surface area of the fiber scaffold developing from inefficient evaporation of the solvent in the PCL solution in the limited space of a closed channel, a drying step was applied by blowing compressed air through the channel for 5 seconds after each coating. The coated fibers were examined using SEM. As shown in SEM images in FIG. 3A, a fibrous substrate was deposited on the inside of a channel. In comparison, the SEM image of a bare channel (FIG. 8A) showed only a ridged surface in the channel area, resulting from the resolution of the 3D printer.

Figures 3A, 3B:
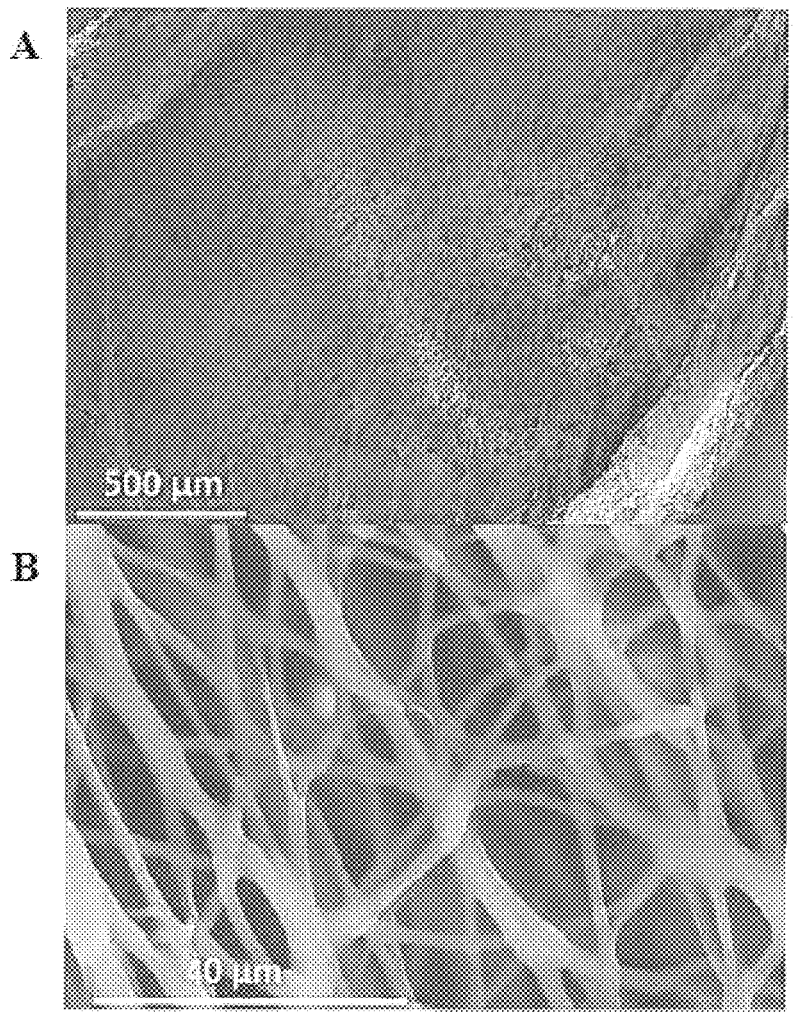
FIG. 3A is a low magnification scanning electron microscope (SEM) image depicting an electrospun fiber scaffold on the surface of the inner wall of a fluidic device.
FIG. 3B is a high magnification SEM image depicting an electrospun fiber scaffold on the surface of the inner wall of a fluidic device.
Figure 3C:
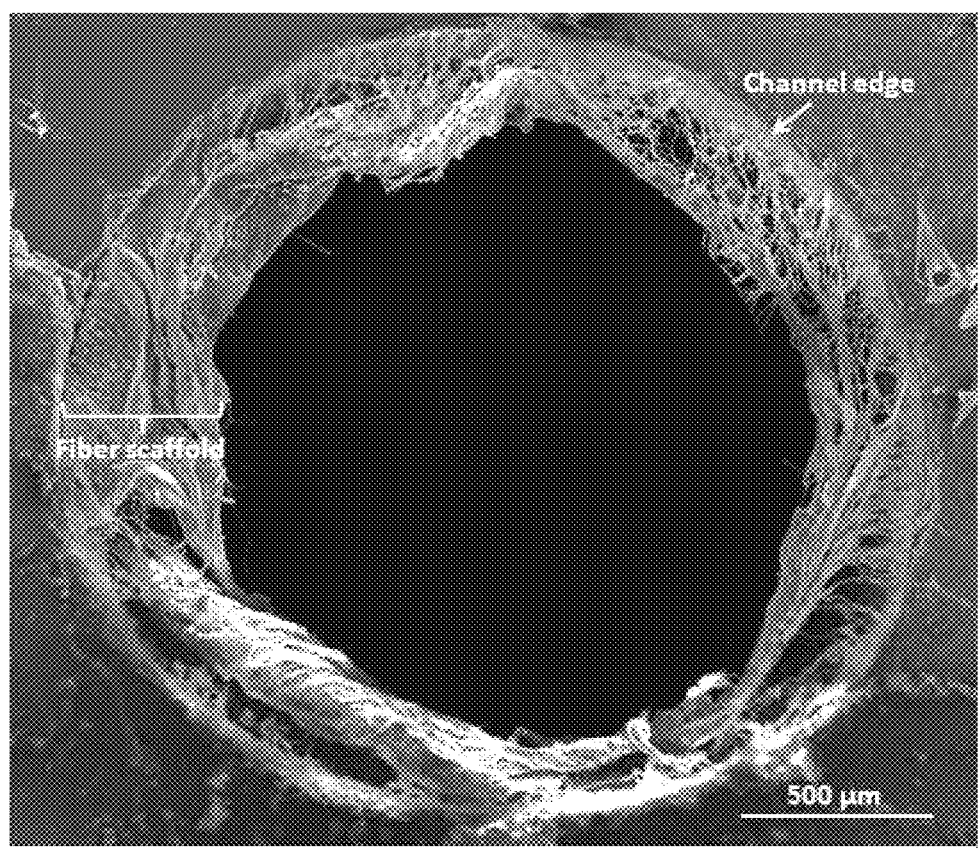
FIG. 3C is a cross sectional SEM image showing the electrospun fiber scaffold extending from the inner wall channel edge toward the lumen of the channel.

FIG. 3B is a SEM image of the fiber scaffold at higher magnification, which clearly shows fine fibers and pores fabricated on the channel surface. ImageJ analyses on the SEM images indicated that the mean fiber size was 1.63±0.57 µm and the average pore size was 113±19 µm$^2$ (mean of 4 samples±standard deviation). FIG. 3C is a cross sectional SEM image showing the fiber scaffold extending from the inner wall channel edge.

Figures 4A, 4B:
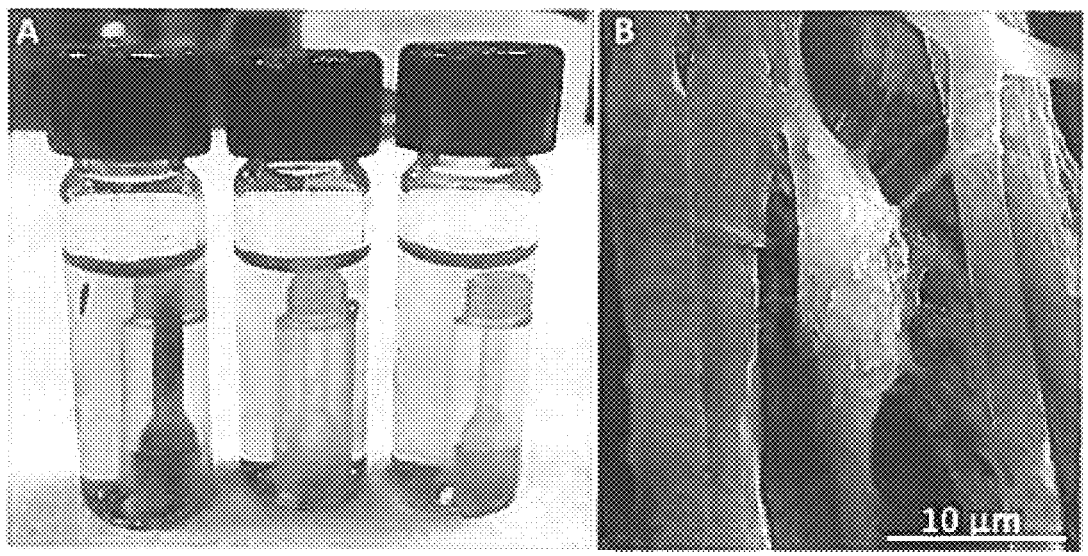
FIG. 4A is a photograph depicting the MTS assay to quantify viable cells in three fluidic devices.
FIG. 4B is a high magnification SEM image of a fibroblast cultured on an electrospun fiber scaffold in a fluidic device.

HDFs were used to test the biocompatibility of the scaffold by a static cell seeding and dynamic culturing process. Three fluidic devices were connected end to end by the printed threads to enhance throughput of cell culture. As shown in FIG. 6A, three devices were placed in a test tube containing an HDF cell suspension for static cell seeding. A hole drilled through the cap facilitated $CO_2$ exchange with the culture media through a piece of porous membrane. After incubating for 12 hours, the devices were removed from the test tube and connected to a piece of Tygon tubing to circulate fresh media through the devices using a peristaltic pump for dynamic HDF culturing (FIG. 6B). Microscopic observation of viable cells using fluorescence imaging was not possible because the 3D-printed fluidic device was translucent without polishing however, other assays were used to evaluate the viability and proliferation of the cultured HDFs, as have been widely used with opaque hollow fiber chambers (HFC). Hollow fiber chambers are large volume (hundreds of mL) perfusion based cell culture devices that are commonly used in pharmaceutical studies and the MTS assay can be used to evaluate cell proliferation in a HFC. MTS assay changes its color form light orange to purple with viable cells, with the purple color intensity being proportional to the amount of viable cells. As shown in FIG. 4A, even though the devices were translucent, a layer of dark purple could be observed on the inside of the left device, which was fiber coated on the inside. This result indicates that proliferative HDFs were successfully cultured on the fibrous scaffold.

Figures 8A, 8B:
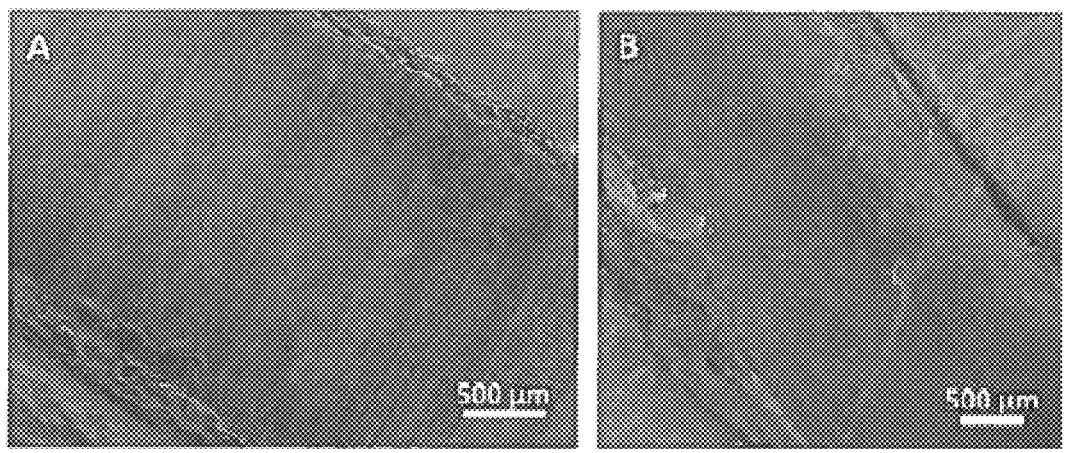
FIG. 8A is a scanning electron micrograph (SEM) image of the inner surface of a bare channel showing ridges in the channel as the result of the 3D-printing process.
FIG. 8B is a scanning electron micrograph (SEM) image of a channel coated by a layer of PCL showing a smooth surface.
Figure 9A:
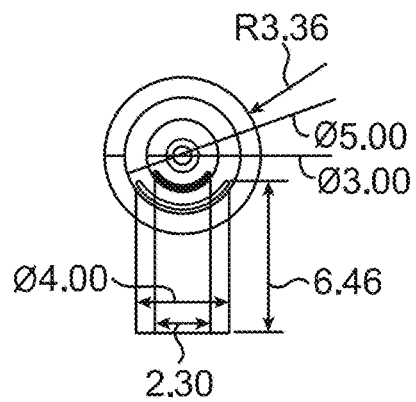
FIG. 9A is a schematic illustration depicting a top view of a 3D-printed air sheath device for focusing fibers during the spinning process and showing exemplary dimensions.
Figure 9B:
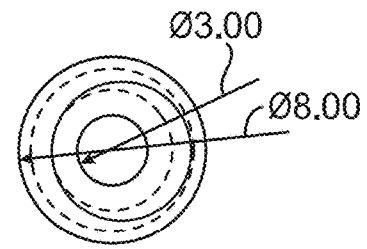
FIG. 9B is a schematic illustration depicting a top view of a 3D-printed air sheath device for focusing fibers during the spinning process and showing exemplary dimensions.
Figure 9C:
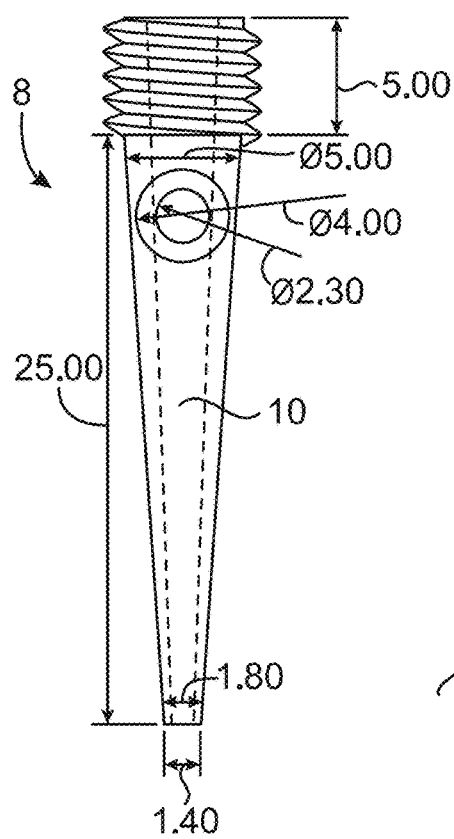
FIG. 9C is a schematic illustration depicting a side view of a 3D-printed air sheath device for focusing fibers during the spinning process and showing exemplary dimensions.
Figure 9D:
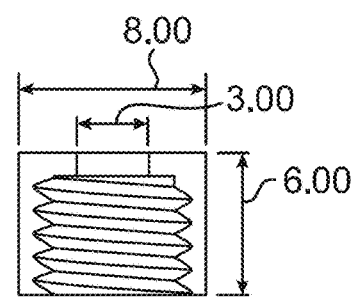
FIG. 9D is a schematic illustration a top view of the thread region and showing exemplary dimensions.
Figure 9E:
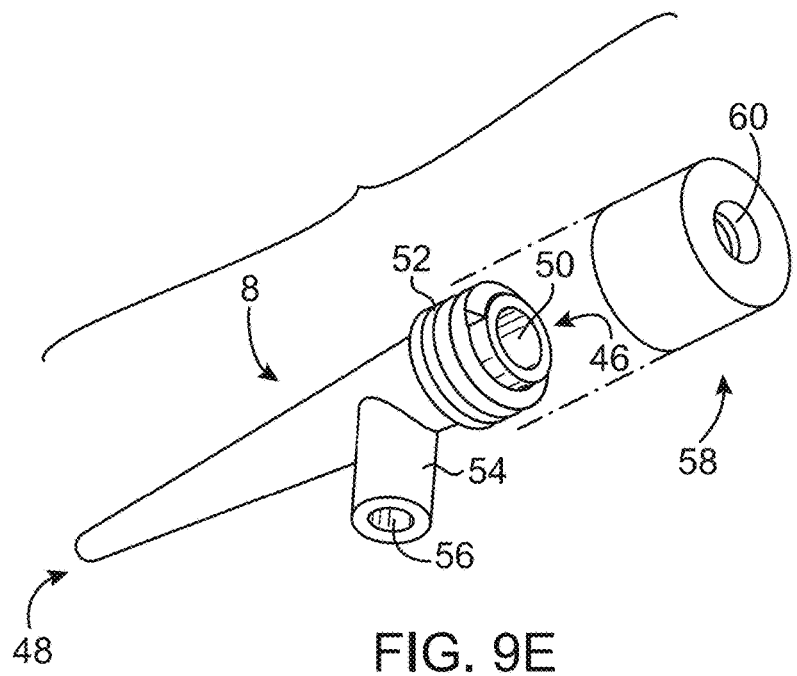
FIG. 9E is a schematic illustration depicting an exploded view of a 3D-printed air sheath device for focusing fibers during the spinning process.

In contrast, HDFs were not cultured on a bare fluidic device (the middle vial in FIG. 4A) or a layer coated device (the right device in FIG. 4A). The layer coated device was prepared by pushing PCL solution through the channel, followed by a drying process in a fume hood. FIG. 8B shows the SEM images of a bare channel and a layer coated channel. The bare channel only showed ridges resulting from the resolution of the 3D-printer, while the PCL layer coated channel lacked fibrous and porous structures, though it was smoother than the bare channel. The purple solution from the first vial in FIG. 4A was then pipetted out for absorption measurement to quantify the amount of viable cells. It was determined that $(4.13±0.76)×10^5$ viable cells were cultured on such a scaffold on the inside of a device (mean of 5 devices±standard deviation). The morphology of the cells was examined by SEM. As shown in FIG. 4B, the spindle morphology and the size of the cell were consistent with in vivo HDFs. Some pseudopodia were also formed by the cells to attach to surrounding fibers, further confirming that the cells adhered to the fibers.

The cells were dynamically cultured on the in-channel scaffold with fresh media being circulated through the devices for 24 hours (FIG. 6B). As discussed above, viable and adhering HDFs were successfully cultured under the flow conditions and no fiber detachment was observed after circulating the media. 3D-printing enables the devices to be rugged and robust, which allows for media circulation at a high speed (400 µL/min) for a long time without structural or functional impairments. Therefore the 3D-printed devices in the work can be potentially developed as a miniaturized alternative to currently commonly used large volume perfusion-based bioreactors (e.g. hollow fiber chambers).

These results demonstrated that the methods and devices of the present disclosure can be used as novel "Cells-on-a-Chip" modules. The devices enable cell culture on a substrate resembling the ECM and cell studies under flow conditions. The application of the air sheath device solved the overspray and deposition problems of electrospun fibers utilizing traditional techniques, and dynamically focused fibers into a fluidic channel. SEM imaging and subsequent ImageJ analyses indicated that fine fibers and porous structures can be constructed on the inside of the channel as a cell culture matrix. The electrospun fibers enabled cell adhesion and proliferation, as well as adopting their physiological morphology. The methods and devices further provide a protocol for cell culture on a fluidic device with flow conditions, which can be applied to "Organs-on-a-Chip" models.

Example 7

In this Example, the fabrication of a poly(dimethylsiloxane) (PDMS) fluidic device and coating the device channel with an electrospun fiber scaffold is described.

A mold was 3D-printed in separate parts as shown in FIG. 10A. The parts were assembled as shown in FIG. 10B and sealed with tape to minimize leakage. A PDMS prepolymer solution (at a ratio of prepolymer:curing reagent of 10:1) was poured into the mold and incubated at 75° C. for 30 minutes for polymerization. After polymerization, the parts of the mold were separated from the cured PDMS device as shown in FIG. 10C. The dimensions of the square shaped channel as determined by the post dimensions of the mold were 2 mm×2 mm and 15 mm in length.

Electrospinning of fibers into the PDMS fluidic device was performed as described in Example 2.

Example 8

In this Example, the culture of HDF cells in poly(dimethylsiloxane) (PDMS) fluidic device was investigated.

PDMS fluidic devices were sterilized as previously described. A suspension of HDF cells was gently pipetted through the channel. The liquid tension held the cell suspension in the channel. The devices were then placed in a 50 mm petri dish, with the addition of fresh media to immerse the devices. The petri dish was then placed in a 37° C. incubator. The HDFs were cultured in this way for 2 days in the PDMS devices.

The HDFs cultured on the fiber scaffold coated in the PDMS channel were rinsed using warm (37° C.) Hanks Balanced Salt Solutions (HBSS, Sigma-Aldrich, MO, USA), after which, 4% formaldehyde solution (in PBS) was pipetted into the channel to fix the cells for 10 minutes at 37° C. After rinsing off the remaining formaldehyde, Alexa ACTINRED™ 555 reagent (LifeTechnology, WA, USA) was used to stain actin of the cells for 20 minutes at 37° C. 4',6-diamidino-2-phenylindole solution (DAPI, LifeTechnology, WA, USA) was used to identify nuclei of the cells during the imaging process using a confocal microscope (Leica, Germany).

Figure 11A:
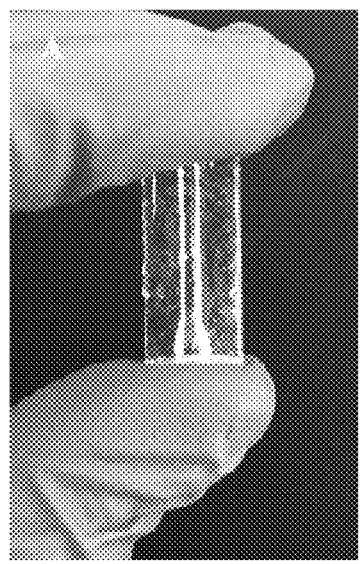
FIG. 11A is a photograph of a PDMS device after being removed from the 3D-printed mold and showing the microchannel.
Figure 11B:
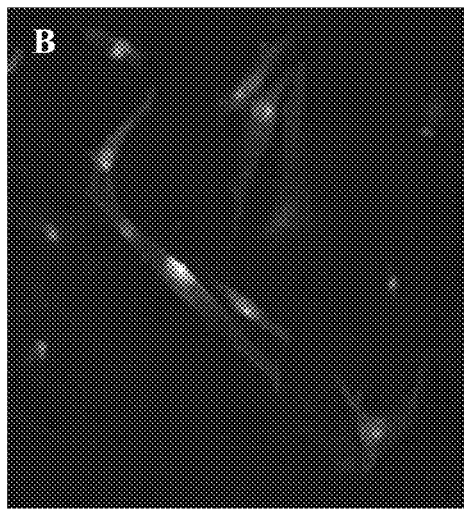
FIG. 11B is an immunofluorescence micrograph of HDF cells cultured on the electrospun fiber scaffold in a PDMS device.
Figure 11C:
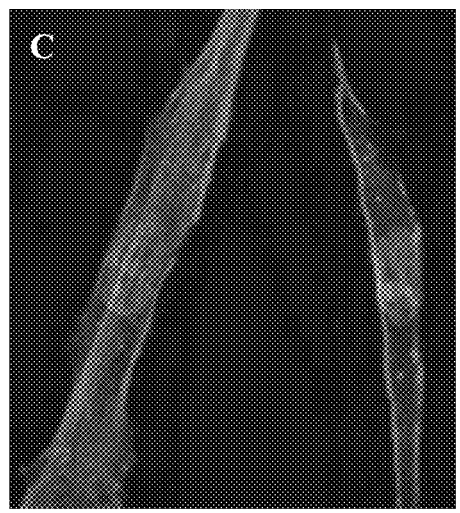
FIG. 11C is a higher magnification immunofluorescence micrograph of HDF cells cultured on the electrospun fiber scaffold in a PDMS device.

As shown in in FIG. 11A, the PDMS device was transparent with the channel being visible with the naked eye. Confocal images of HDF cells cultured on the electrospun fiber scaffold showed actin filaments (red staining) and nuclear staining (green) of viable cells. These results demonstrate the feasibility of optical observation and imaging of cells cultured on fibrous scaffolds inside the fluidic device.

Example 9

In this Example, fluidic devices having fiber scaffold inserts were prepared and used for cell culture.

Figure 13A:
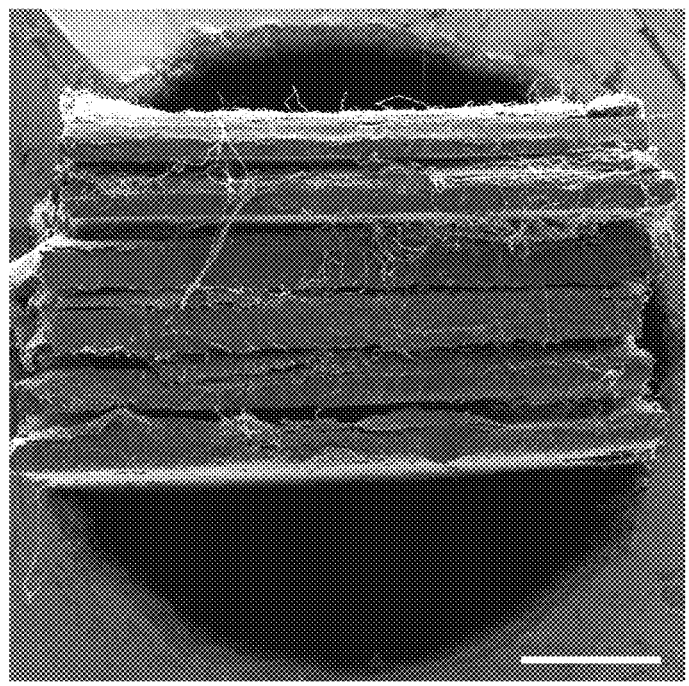
FIG. 13A is a scanning electron micrograph showing an end view of an exemplary embodiment using six stacked fiber scaffold inserts.
Figure 13B:
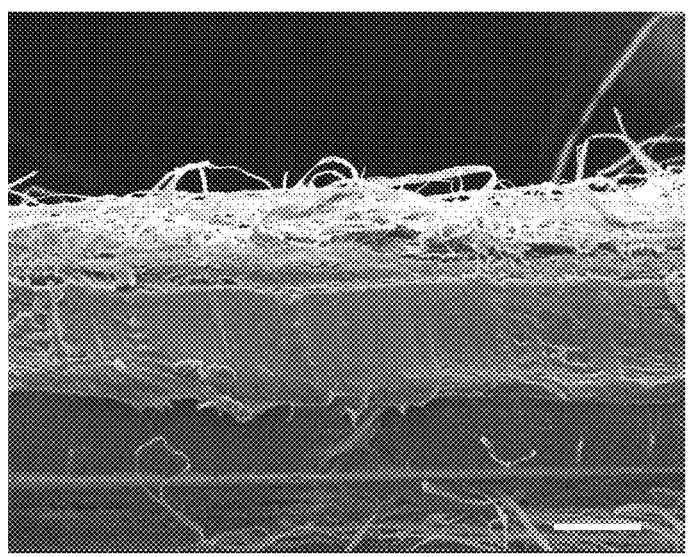
FIG. 13B is a scanning electron micrograph of an enlargement of the end view of the top single fiber scaffold insert in FIG. 13A.

As illustrated in FIG. 12, fiber scaffolds were prepared by electrospinning and collected on a flat plastic sheet. After deposition of the fiber scaffold, the fiber scaffold was cut to a shape matching the channel of the fluidic device to form fiber scaffold inserts that were inserted into the fluidic device. FIG. 13A is a scanning electron micrograph showing an end view of six stacked fiber scaffold inserts. FIG. 13B is a scanning electron micrograph showing an end view of a single fiber scaffold insert. Fluidic devices were seeded with macrophages and compared to macrophages cultured on flat inserts. FIG. 14A is a scanning electron micrograph showing macrophages cultured on fiber scaffold inserts that were inserted into the fluidic device. FIG. 14B is a scanning electron micrograph showing macrophages cultured on a flat plastic sheet.

Example 10

In this Example, solution blown spinning was used to prepare fluidic devices and used for cell culture.

Two types of polymers were studied: PCL and PS. For the PCL study, a PCL solution was made by dissolving PCL beads (MW=80,000, Sigma-Aldrich, MO, US) in 1,1,1,3,3,3-hexafluoro-2-propanol (HFP), and this solution was loaded in a 500 µL glass syringe. Multiple concentrations (w/v) of PCL were analyzed. A piece of Tygon tubing (0.02" i.d.×0.06" o.d., Cole-Parmer, IL, US) was connected to the syringe by Luer adapters (IDEX, CA, US). At the other end of the Tygon tubing, a steel cannula (300 µm i.d.×550 µm o.d., New England Small Tube Corporation, NH, US) was connected as the outlet for the polymer solutions. The cannula was then placed in a 3D-printed gas sheath device, which is the key part in the solution blow spinning technique. The gas sheath device includes a cone with a side connection port to a gas tank, and an open cap. The cap and the cone were joined with the printed threads, with a piece of septa in between. After the steel cannula was placed through the gas sheath device, the side port of the sheath device was connected to a N2 tank to apply a sheath flow surrounding the cannula, which tapers the solution to form a cone. Different sheath flow velocities were tested for different PCL concentrations in this study, as will be described subsequently. A syringe pump (Harvard apparatus, MA, US) was used to push PCL solutions at 10 µL/min through the cannula, where the sheath gas sharpened the polymer solution to form a cone, which then bursts into fine fibers. Unlike electrospinning, the collector substrate does not need to be grounded in this technique. Therefore, any substrate can be used as the collector. Substrates such as card paper and petri dishes can be used to collect fibers in this study.

For the PS studies, polystyrene beads (MW=280,000, Sigma-Aldrich, MO, USA) were first dissolved in dimethylformamide (DMF, Sigma-Aldrich, MO, USA), with this 20% (w/v) solution being used to make more dilute solutions of different concentrations. To form the fibers, a PS solution was then drawn in to a 3 mL syringe, which was fitted with a 20 gauge blunt tip needle. A steel cannula (300 µm i.d.×550 µm o.d.) was then inserted into the tip of 20 gauge needle as the outlet of the polymer solution. The syringe was placed in a syringe pump that was situated vertically and the same gas sheath device was fitted over the cannula. The PS solution was then delivered at a flow rate of 75 µL/min With applied sheath $N_2$ around the cannula, PS fibers can be generated and collected.

The sheath $N_2$ influenced fiber generation from polymer solutions. The highest PCL concentration used was 12% (w/v); more concentrated solutions appeared too viscous to be delivered by a regular syringe pump. Sheath $N_2$ with decreased pressures (from 20 psi, at a decreasing interval of 2.5 psi) was applied to the 12% PCL solution. The highest pressure at which a stable cone was formed was recorded as the upper limit of the sheath $N_2$ velocity window. As the sheath $N_2$ pressure decreased, the polymer solution tended to form droplets instead of cones at the end of the cannula. The lowest pressure at which a cone can still form (below which, droplets will form) was recorded as the lower limit of the sheath $N_2$ window.

The concentration of PCL was then serially lowered by 2% (w/v), and the same sheath tests were performed, until the solution was too diluted to generate fibers even at a low sheath $N_2$ velocity, which indicated the threshold concentration to generate fibers. The sheath $N_2$ pressure values (in psi) were converted to linear velocity values (in m/s) by using a tube flowmeter (model 7205-0062-A, King Instrument Company, CA, US). Different polystyrene solutions (12.5%, 15%, 20% (w/v)) were examined in a similar way to acquire the sheath flow velocity range.

Solution blow spun fibers generated from different polymer concentrations and at different sheath $N_2$ flow velocities were characterized by scanning electron microscope imaging (SEM, FEI Inspect-50 model, OR, USA). After the fiber containing substrates were cut into about 1 cm×1 cm squares, samples were sputter coated with gold at 30 mA for 40 sec (Denton Vacuum LLC, NJ, USA) to increase conductivity. After a sample was loaded in the SEM, an accelerating voltage of 20 kV was applied. At least 3 images from each sample were taken from randomly chosen spots. The SEM images were analyzed using the ImageJ program. For each image, at least 50 fiber diameter measurements were taken. Repeating measurements on the same fiber were avoided to the maximum extent.

Figure 16A:
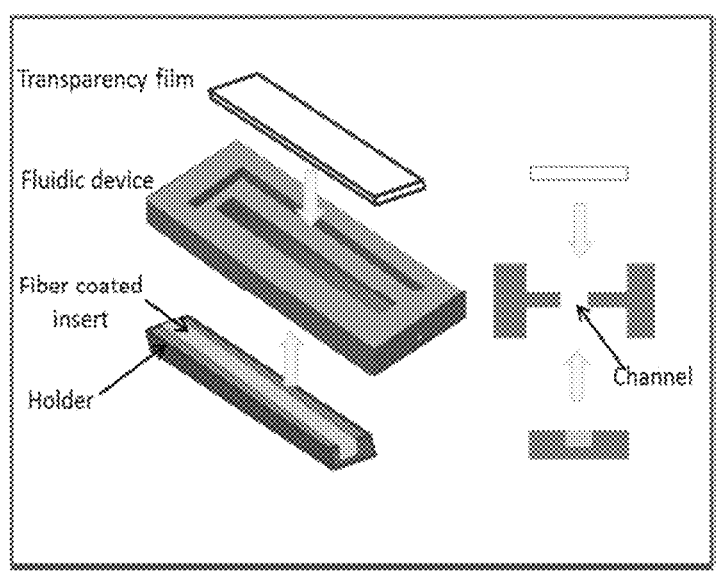
FIG. 16A is a schematic depicting assembling of an exemplary device using blown spun fibers. A 3D-printed rectangular insert was first coated with solution blow spun fibers and then fit into a holder. A fluidic device was also fabricated by 3D-printing, which has two slots on top and bottom sides (only the top slot is visible). The holder was then plugged into the bottom slot; while a piece of transparency film was placed in the top slot (super glue was used to fix the film on the device). The right panel shows the side view of the process. There is a void space between the slots, which will form the channel when both sides are sealed.
Figure 16B:
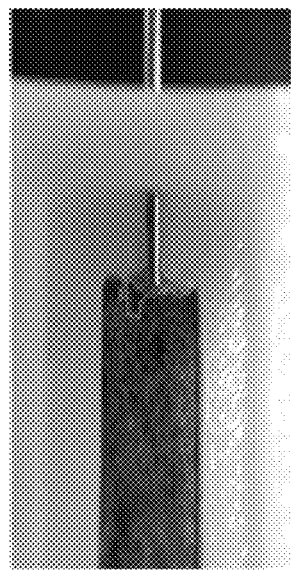
FIG. 16B is a photograph showing a zoomed in view of the fluidic channel with white fibers clearly seen in the channel area. To take the photograph, black tape was placed in the channel to better show the fibers coated on it but this was not used in cell culture experiments (the tape was for contrast).
Figure 16C:
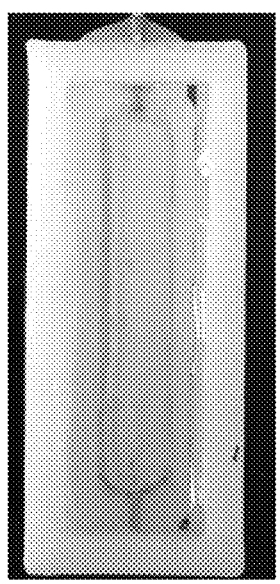
FIG. 16C is a photograph of an assembled device filled with DMEM media for cell culture.

The effect of a 3D scaffold on macrophage culture was analyzed using a 3D-printed microfluidic device, onto which fibers were solution blow spun for 3D cell culture under flowing conditions. The device was 3D-printed with a Mojo 3D-printer (Stratasys, MN, USA) with Acrylonitrite Butadiene Styrene (ABS, Sigma-Aldrich, MO, USA) material. FIG. 16 shows the assembling of the device. First, PCL fibers were spun onto an ABS insert (5 mm width×25 mm length×2.5 mm thick), after which the insert was fitted into a holder (10 mm wide×30 mm long×4.5 mm thick with a 2.5 mm; "Holder" in the figure). Finally, the holder with the insert was plugged into the bottom slot of the flow device (the upward arrow in the figure). The flow device had another slot on the top side, where a piece of transparency film was placed (epoxy was used to affix film; the downward arrow in the figure). As shown in the side view (the right panel of the figure), a rectangular space between the two slots of the flow device defines the channel when both slots were sealed. The assembled flow device's channel has dimensions of 1 mm tall, 5 mm wide, and 25 mm long (5 mm$^2$ cross-sectional area). In order to visualize the fibers and cells in the device, the flow device was fitted with a window made from transparency film and was set in place with epoxy (Permatex, CT, USA). The flow device has a steel pin (20 gauge, CML Supply, KY, USA) inserted into a hole designed within such that tubing can be attached. As a control, fibronectin (1 mg/L in PBS) coated inserts were also prepared and assembled in the fluidic device.

The mouse macrophage cell line RAW 264.7 was used in to study cell culture on the fiber-containing microfluidic device. After scraping a near confluent layer of the cells off a 35 mm petri dish, the cells were centrifuged at 500 g for 5 min and then re-suspended in DMEM media containing 10% fetal bovine serum (FBS) and 1% antibiotic (pen-strep). The cell suspension (~2×106 cells/mL) was then introduced into the assembled fluidic device via tubing and a syringe until the channel was completely filled, after which, the device was placed in a petri dish and incubated (37° C., 5% CO$_2$) for 24 hours. After the 24 hour cell culture, macrophages were stimulated by circulating media containing lipopolysacchride (LPS). A piece of Tygon tubing (2 feet, 0.02"i.d.×0.06" o.d., Cole-Parmer, IL, US) was attached to the steel pin and fed through the peristaltic pump. The assembled flow device with cells was situated on the top of a 15 mL centrifuge tube and the opposite end of the tubing was placed in the bottom of the tube. A solution of 0.1 mg/mL of LPS in DMEM (phenol red free; Life Technologies, CA, USA) was prepared and 1.3 mL was placed into the centrifuge tube. The device was placed into the incubator and the media was circulated at 400 µL/min for 24 hours. The experimental setup is shown in FIG. 16.

Nitrite (NO$_2$) was detected as a pro-inflammatory biomarker of macrophages using UV-vis spectroscopy with Griess reagents. An aliquot of 200 µL of the circulated media was pipetted into a clear 96 well plate (Greiner, Sigma Aldrich, MO, US), with 50 µL of Griess reagent for nitrite (Fluka, Sigma Aldrich, MO, US) being added and mixed. After 15 minutes of reaction, the well plate was read using a plate reader (Molecular Devices, CA, US) using absorbance at 530 nm. A calibration curve was obtained for each run using a nitrite standard solution (Sigma-Aldrich, MO, US) diluted with fresh stimulation media. Because cell count on each device may vary, the nitrite release from each device was normalized in terms of the total cell count. In order to quantify the amount of cells cultured on each device, after the LPS stimulation, the device was soaked in 1 mL DI water in a 1.7 mL centrifuge vial, which was then vigorously vortex mixed for approximately 10 minutes to ensure complete cell lysis. The Hoescht assay was then prepared to quantify the amount of DNA, which can be a measurement of cell count. Stock Hoesct 33258, pentahydrate (Life Technologies, OR, US) was first diluted from 10 mg/mL to 0.02 mg/mL with THE buffer (42 mM Tris-HCl, 4.2 mM EDTA, and 8.4 M NaCl; all chemicals were from Sigma-Aldrich, MO, USA). In a 96 well plate, 40 µL of the prepared Hoescht assay and 160 µL of the cell lysate was added together immediately before analysis with the plate reader under fluorescence mode (excitation=350 nm, emission=460 nm) A calibration curve was constructed for this by counting cells with a hemocytometer first, lysis in DI water, and analysis with the Hoescht method.

PS fibers were coated on the 3D-printed ABS insert mentioned above via solution blow spinning (20% PS; sheath N2 pressure=15 psi). Four fiber-coated inserts were sterilized by soaking them in 70% ethanol and subsequent drying in UV, which were then placed in a 5 cm petri dish, followed by adding 5 mL of 1.6×106/mL endothelial cell suspension (in fresh DMEM) in a sterile hood. The petri dish was then placed in a 37° C. incubator for 24 hours for the cells to adhere on the fibers (static culture), after which, the inserts were assembled into the fluidic devices as have described above. Fresh media was then circulated through each device via the connected Tygon tubing using a peristaltic pump at 400 µL/min for designated periods of time (dynamic culture) for up to 48 hours. Cells were examined after staining with acridine orange at pre-determined time points with a fluorescent microscope and counted using the Hoescht method as described above.

To solution blow spin PCL nanofibers (using the 3D printed gas sheath device), the PCL solution was pumped through Tygon tubing and the steel cannula, sheath N$_2$ was applied around the cannula through a 3D-printed gas sheath device. The sheath N$_2$ tapered the PCL solution at the tip of the cannula to form a cone. Like the Taylor cone formed in electrospinning, the cone formed by the sheath N$_2$ expanded at the tip to generate fibers. The fibers were focused by the sheath N$_2$ as they traveled to the collecting substrate.

A 3D-printed gas sheath device was developed that played three roles in the process of solution blow spinning: 1) tapered the polymer solution to form a cone, 2) confined the generated fibers to be deposited as a focused sheet, and 3) aided in the evaporation of the solvent to produce dry fibers on the collector. The size of the tip of the sheath device was also analyzed. The o.d. of the steel cannula was 550 µm, and the gas sheath tip size was determined to be 800 µm in diameter. A smaller tip size led to limited space between the gas sheath and the cannula appeared to cause N$_2$ flow problems out of the device, while the N$_2$ flow out of a larger tip size did not taper the polymer solution as effectively. With a rotating collection stage, a round fiber sheet with diameter of about 1 cm could be collected reproducibly. The sheath N$_2$ also dried the solvent of the polymer solution. If the gap distance (distance between the cannula and the collector) is larger than 4 cm, all the collected fibers collected were dry, with no welded fibers being observed. Fibers spun from a 12% (w/v) PCL solution under sheath N$_2$ flow at 3.1 m/s (12.5 psi) clearly demonstrates the creation of clean, non-welded PCL nanofibers with the solution blow spinning technique using the 3D printed sheath device.

Figures 17A, 17B:
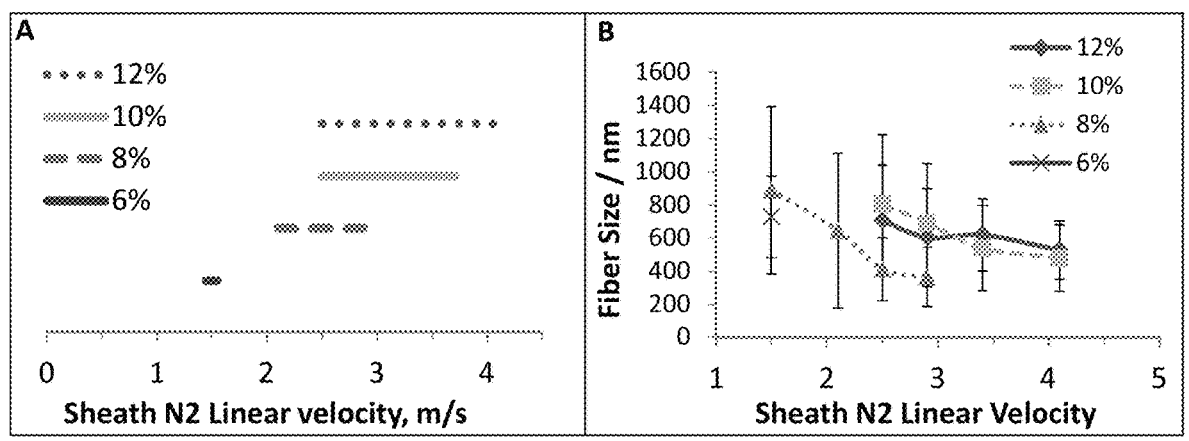
FIG. 17A is a graph depicting sheath $N_2$ velocity windows for different PCL concentrations using the 3D printed sheath device for fiber generation.
FIG. 17B is a graph depicting widths of fibers from different PCL concentrations at their specific sheath $N_2$ velocity windows. (N=9 samples, error=standard deviation). PCL solutions with higher concentrations had larger sheath $N_2$ velocity windows. For each concentration of PCL, the fiber size tended to decrease with increased sheath $N_2$ flow velocity.

The sheath N$_2$ velocity highly affected the formation of cones and subsequent fibers. Too high of a sheath N$_2$ velocity led to unstable cones, where the cone/fibers drifted in random directions, while too low of a velocity did not taper the solution into a sufficient cone, with the solution instead forming droplets when exiting the cannula. The most concentrated PCL used in this example was 12%. Higher concentrations led to viscous solutions that were difficult to pump. A 4.1 m/s (20 psi) N$_2$ sheath flow was initially applied to the PCL solution, which was then serially decreased at an interval of 1.5 m/s (2.5 psi) until the first stable cone was observed, with this indicating the upper limit of the window for fibers from a 12% PCL solution. As the sheath N$_2$ velocity decreased to a point where cone formation failed to occur (and only droplet formation was observed), the lower limit of the window was determined. The PCL concentration was serially lowered by 2%, and the sheath N$_2$ velocity window for each concentration was determined, the results of which are summarized in FIG. 17A. A higher concentration of PCL had a larger sheath $N_2$ velocity window. The 6% PCL solution (viscosity=505.2±0.76 cP) was determined as the lower threshold concentration, below which no fibers were generated even with a very low sheath $N_2$ velocity. The cone was formed by the balance between sheath $N_2$ focusing force and the viscous force of the polymer solution. The sizes of fibers generated from different concentrations of PCL at their specific sheath $N_2$ velocity windows were measured on SEM images using ImageJ. FIG. 17B demonstrates that solution blow spinning could generate fine fibers on the scale of hundreds of nanometers for all 4 PCL concentrations used. With increased sheath $N_2$ velocity, the fiber size tended to decrease. The sheath $N_2$ flow velocities used in this technique were achieved with commonly used gas cylinders and associated tubing, which have been routinely used in applications such as sample dehydration and polymer production.

Figures 18A, 18B, 18C, 18D:
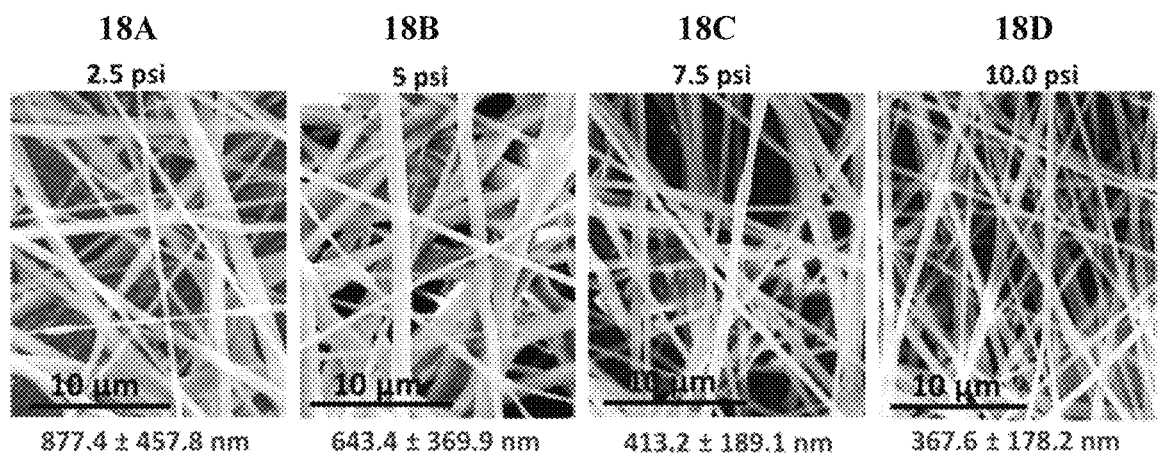
FIG. 18A-18D are scanning electron micrographs depicting images of solution blow spun fibers from 8% PCL solutions at different sheath $N_2$ linear velocities. The numbers under each image indicate the measured fiber sizes (mean of 9 samples±standard deviation). From left to right, the sheath $N_2$ flow velocities are 1.5, 2.1, 2.5, 2.9 m/s, respectively (corresponding pressure values are 2.5, 5.0, 7.5, and 10 psi). The photographs show that the fiber size decreased with increased sheath $N_2$ linear velocity, as did the deviation of fiber sizes.

To better visualize how the sheath $N_2$ affected PCL fiber size/morphology in the 3D printed gas sheath device, SEM images of fibers generated from 8% PCL under 1.5, 2.1, 2.5 and 2.9 m/s sheath $N_2$ flow (corresponding pressure values are 2.5, 5.0, 7.5, and 10 psi) were captured (from left to right in FIG. 18). As indicated by the numbers below the images, which are the measured sizes for corresponding fibers (mean of 9 samples±standard deviation), the fiber size tended to decrease with increased sheath $N_2$ flow. The fiber sizes shown in FIG. 18C (2.5 m/s sheath $N_2$) and FIG. 18D (2.9 m/s sheath $N_2$) are statistically smaller than that in FIG. 18A (1.5 m/s sheath N2) at 95% and 99% confidence levels, respectively. These images also suggest that with a higher sheath $N_2$ velocity, the fiber size became more uniform, as indicated by the decreasing standard deviation values.

As aforementioned, micro/nano fibers have applicability in a number of fields. Because the collector does not need to be grounded, any substrate such as metals, paper, and plastics can be coated with fibers directly by solution blow spinning. For all the applications in this work, 12% PCL at 10 psi $N_2$ sheath pressure were used. The fiber deposition process lasted 2 min, which generated a fiber film of around 20 μm. The thickness increased with deposition time, until the upper limit is reached, beyond which, the newly formed fibers start to delaminate off the film and thus cannot be further deposited. With the 3D printed gas sheath device it was found that the maximum thickness of the PCL fiber film under these conditions is 178±14 μm. Fibers were directly coated on a 35 mm petri dish by solution blow spinning, which was then used as a scaffold for in vitro cell/tissue culture. Because petri dishes and other plastic cell culture containers are not conductive, such fibers cannot be directly coated on them by the conventional electrospinning technique. Instead, a commonly used method is to electrospin fibers onto a grounded metal substrate (usually forms a wide spread fiber sheet), which can be peeled off, cut, and placed in a dish for cell culture. PCL fibers were successfully coated in a 6-well cell culture plate by solution blow spinning.

Figures 19A, 19B:
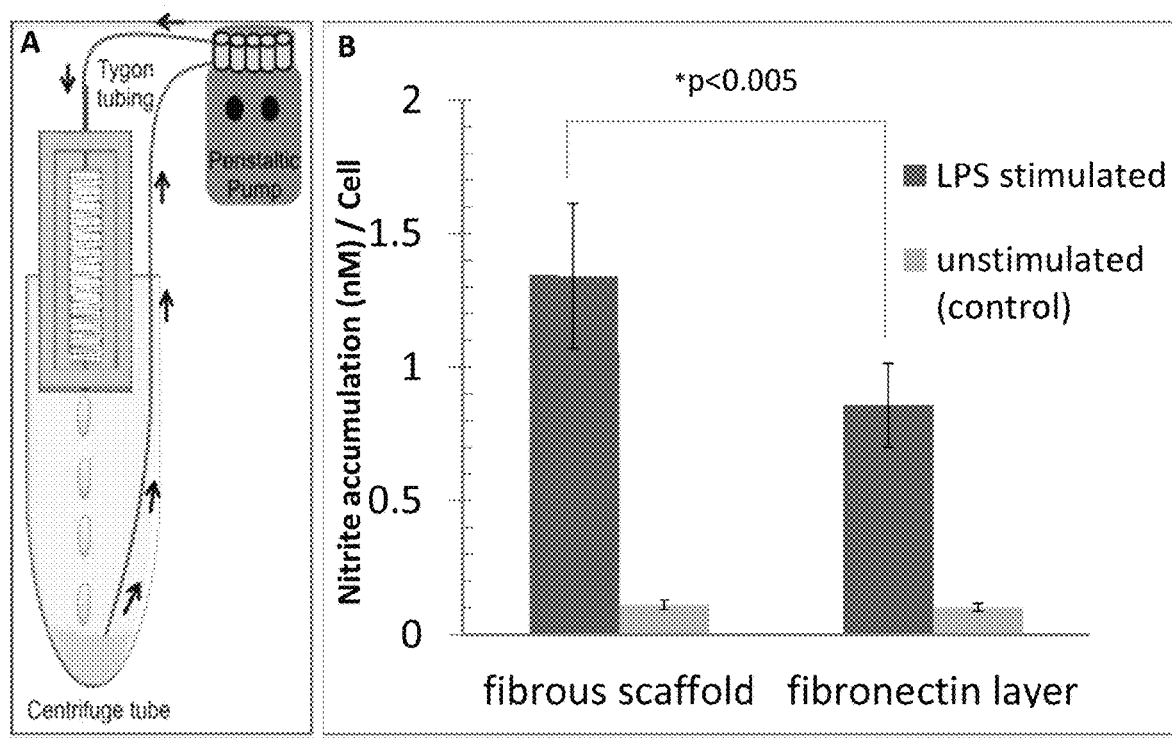
FIG. 19A is a schematic depicting the experimental setup for macrophage stimulation. Tygon tubing was fixed over the steel pin in the flow device. The Tygon tubing was fed through a peristaltic pump and the loose end was placed into a centrifuge tube. The flow device was positioned in the top of the centrifuge tube and 1.3 mL of 0.1 mg/mL LPS in complete DMEM without phenol red was dispensed into the centrifuge tube for 24 hour circulation.
FIG. 19B is a graph depicting the comparison of nitrite release of macrophages cultured on PCL fibers and fibronectin coated inserts. After being stimulated by LPS, macrophages in the microfluidic devices produced significantly more nitrite per cell when cultured on PCL fibers relative to those cultured on a flat surface (1.35±0.27 vs. 0.86±0.16 nM/cell, dark grey bars, $p<0.005$, n=6, error=SEM). As a control, macrophages in a device that were not stimulated with LPS produced a small amount of nitrite (0.11±0.02 vs. 0.10±0.01 nM/cell, light grey bars, n=4, error=SEM).
Figure 20A:
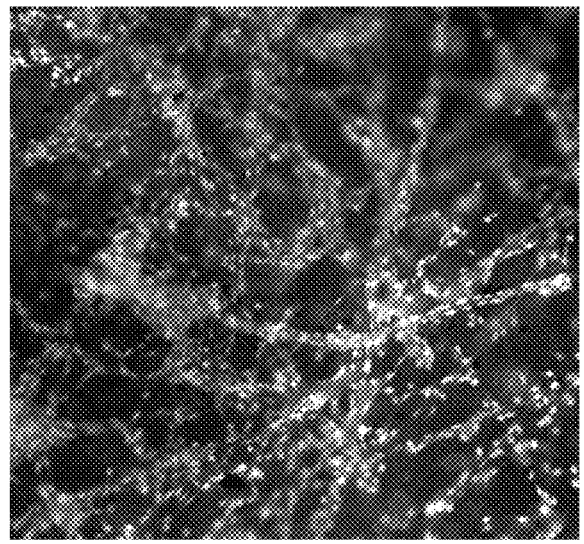
FIGS. 20A-20D depict fluorescent images and cell counting of endothelial cells cultured on PS fibers integrated in the microfluidic device.
Figure 20B:
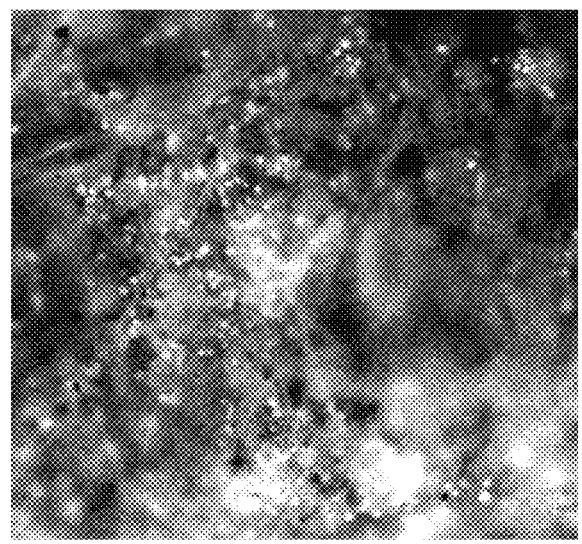
Figure 20C:
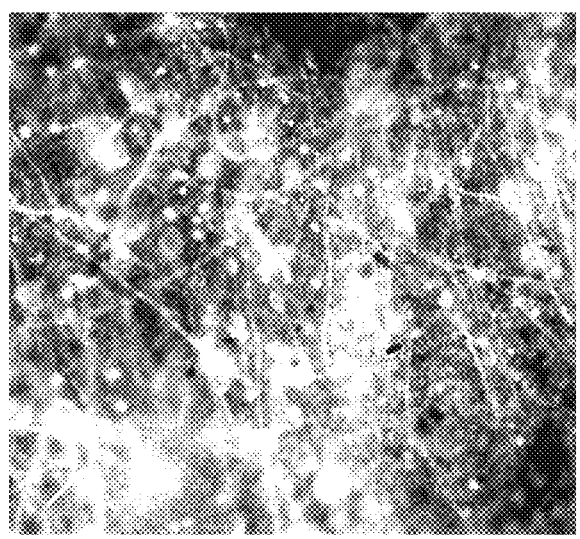
Figure 20D:
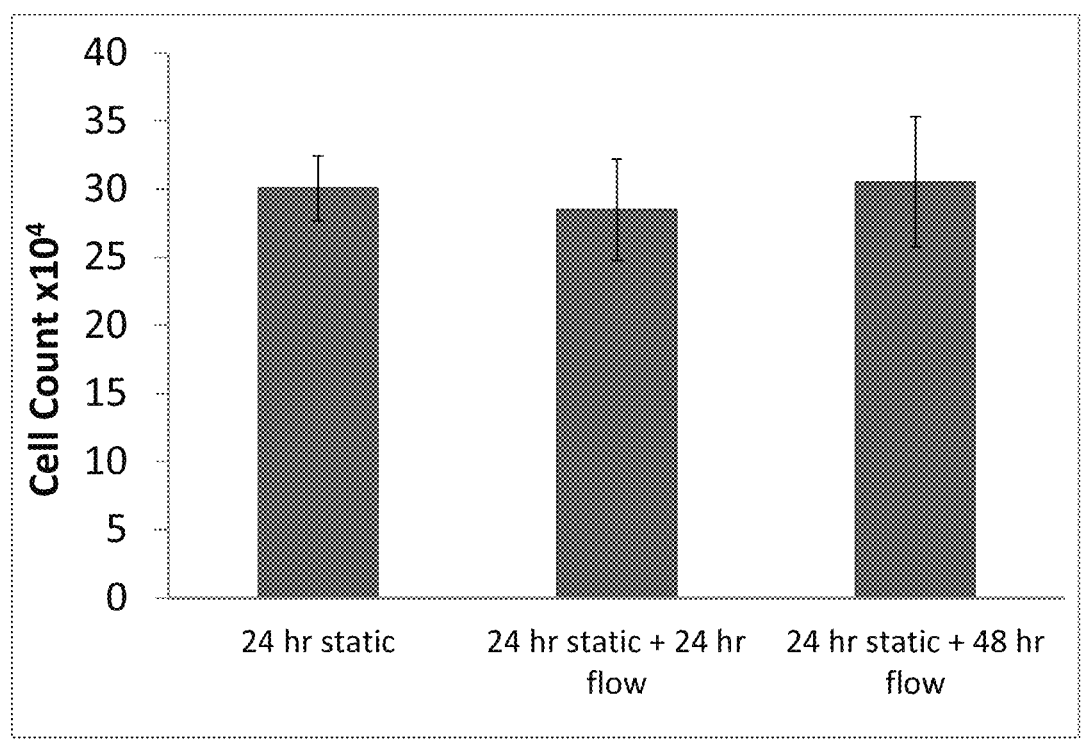

To demonstrate the applicability of the blow spun fibers for microchip-based 3D cell culture, macrophages were utilized (illustrated in FIG. 19A). After culturing macrophages on the devices for 24 hours (static condition), LPS stimulation was introduced to the macrophage cells under flowing conditions. The accumulation of $NO_2^-$ from macrophages cultured on both devices (fibrous insert and flat insert) was measured off-chip using Griess reagent. As macrophages are stimulated, they will transition the phenotype from M0 (native state) to M1 (pro-inflammatory) and then M2 (pro-healing), with the release of various cytokines and other molecules. Reactive nitrogen species (i.e., nitric oxide) is an indicator of the M1 pro-inflammatory state, which will become $NO_2^-$ in cell culture (due to oxidation of the NO). In other words, the amount of accumulated $NO_2^-$ can be a biomarker of the pro-inflammatory response of macrophages. Because the cell count on different devices may vary, the amount of cells on each device was also determined using a Hoescht assay, as described in the Experimental section (cell count data). The measured $NO_2^-$ from each device was then normalized by cell count on that specific device (presented as nM NOT per cell; nM/cell). FIG. 19B shows the normalized $NO_2^-$ accumulation from macrophages cultured on fibers and on the flat, fibronectin-coated surface. It can be seen that after LPS stimulation there was significantly more $NO_2$ release (dark grey bars in FIG. 19B; 1.35±0.27 vs. 0.86±0.16 nM/cell; n=6, ±SEM; p<0.005) from macrophages cultured on the fibers in a fluidic channel than those on the flat surface, which indicated that the fibrous scaffold in the fluidic device enhanced the immune response of macrophages upon LPS stimulation. However, the $NO_2$ production from unstimulated macrophages is at a low concentration for both the fibrous and the flat culture conditions, with no significant difference between the two (light grey bars in FIG. 19B; 0.11±0.02 vs. 0.10±0.01 nM/cell; n=4, ±SEM). These results highly indicated that the integrated solution blow spun fibers in the fluidic device provides an improved in vitro ECM mimic for macrophages, as compared to more traditional 2D culture. In addition to fiber integration, some other unique characteristics of this fluidic system make it a versatile tool for future cell studies. Many other cell types can be cultured on the scaffold under flowing conditions. By modulating the insert size and flow rate, specific shear stress can be applied on the cells. For example, endothelial cell culture were tested on a similar fluidic device with solution blow spun PS fibers, which showed good viability of the cells. FIG. 20A shows the fluorescent image of the endothelial cells on the PS fibers after a 24-hour static culture (in a petri dish, with initial seeding being very concentrated), after which, the cells were cultured for another 24 and 48 hours under flowing conditions (FIGS. 20B and 20C, respectively). A comparison between the three fluorescent images did not indicate difference of cell counts, meaning that no cells were lost during this pumping experiment. The ability to keep the cells adherent for this long period of time in the microchip-based 3D scaffold is a good testament of the improved culture conditions provided by this approach. After accurately quantifying the cells cultured under the three conditions using the Hoechst assay, it was confirmed that the cells were viable on the fibers in the flowing media for at least 48 hours (after the initial 24-hour static culture step, see FIG. 20D). The 3D printed microchip device is also modular, with the insert being removable and easy to reassemble, which enables reusability of the fibrous scaffolds. Although the device used in this Example had a relatively big channel size (1 mm tall, 5 mm wide, and 25 mm long), smaller versions can be made. For example, a device that was made having a 500 μm wide by 1 mm tall (cross section) channel.

The results presented herein demonstrate methods for preparing electrospun fiber scaffolds and blow spun fiber scaffolds to coat fluidic devices such as 3D printed insert. Also disclosed are methods for preparing fiber scaffold inserts for use in fluidic devices. The fluidic devices can be integrated into a fluidic system for 3D cell culture and stimulation under flowing conditions.

What is claimed is:

1. A method for preparing a fluidic device comprising an electrospun fiber scaffold on an inner wall surface of the fluidic device, the method comprising:
providing a fluidic device, the fluidic device comprising: an inlet end, an outlet end, an outer wall, an inner wall, and a channel, the channel defined therethrough by the inner wall and extending between the inlet end and the outlet end; and
selectively coating an inner surface of the inner wall of the fluidic device by placing one of the inlet end or outlet end of the fluidic device proximate to a cannula of an electrospun fiber spinning apparatus, wherein the electrospun fiber spinning apparatus comprises a gas sheath device;
applying gas flow to the gas sheath device;
pumping a polymer solution through the cannula of the electrospun fiber spinning apparatus to prepare a plurality of electrospun fibers;
directing the plurality of electrospun fibers into the fluidic device, wherein the plurality of electrospun fibers form an electrospun fiber scaffold on the inner wall surface of the fluidic device.

2. The method of claim 1, wherein all of the inner wall surface comprises the plurality of electrospun fiber scaffolds.

3. The method of claim 1, wherein the inlet end further comprises threads.

4. The method of claim 1, wherein the outlet end further comprises threads.

5. The method of claim 1, further comprising contacting the fluidic device with a cell suspension.

6. The method of claim 1, wherein the electrospun fiber diameter ranges from 10 nm to 2.5 µm.

7. The method of claim 1, wherein the distance from the cannula to the fluidic device inlet is 2 millimeters.

8. The method of claim 1, wherein the inner wall of the fluidic device is selectively coated from 1 time to 10 times.

9. The method of claim 1, wherein the inner wall of the fluidic device is selectively coated for a time ranging from 1 second to 20 seconds.

10. The method of claim 1, further comprising a drying step after the coating step.

11. The method of claim 1, wherein the electrospun fiber scaffold comprises a pore size ranging from 90 $\mu m^2$ to 135 $\mu m^2$.

12. The method of claim 1, wherein the polymer solution comprises a synthetic polymer, a natural protein and combinations thereof.

* * * * *